United States Patent
Brömme et al.

(10) Patent No.: US 6,544,767 B1
(45) Date of Patent: Apr. 8, 2003

(54) CATHESPIN O2 PROTEASE

(75) Inventors: Dieter Brömme, San Bruno, CA (US); Kathleen Okamoto, Mountain View, CA (US)

(73) Assignee: Axys Pharmaceuticals, Inc., Wilmington, DE (US)

( * ) Notice: Subject to any disclaimer, the term of this patent is extended or adjusted under 35 U.S.C. 154(b) by 0 days.

(21) Appl. No.: 08/536,861

(22) Filed: Oct. 2, 1995

Related U.S. Application Data

(63) Continuation-in-part of application No. 08/330,121, filed on Oct. 27, 1994, now Pat. No. 5,736,357.

(51) Int. Cl.$^7$ .................................................. C12N 9/64
(52) U.S. Cl. ...................... 435/226; 435/219; 435/183; 530/350; 424/94.63; 424/94.65
(58) Field of Search .................................. 435/226, 183, 435/219; 424/94.63, 94.65; 530/350

(56) References Cited

U.S. PATENT DOCUMENTS 5,501,969 A  3/1996  Hastings et al. .......... 435/240.2

FOREIGN PATENT DOCUMENTS

| WO | 9524182 | 9/1995 |
| WO | 9747642 | 12/1997 |

OTHER PUBLICATIONS

Darnell et al., Molecular Cell Biology, Scientific American Books, New York, pp. 954–957, 1986.*
Vernet et al., J. Biol. Chem. 270:10838–10846, May 1995.*
Bromme et al., J. Biol. Chem. 268:4832–4838, Mar. 1993.*
Tao et al., Arch. Biochem. Biophys. 311:19–27, May 1994.*
Smith et al., J. Biol. Chem. 264:20487–20495, Dec. 1989.*
Smith et al. *J. Biol. Chem.* 264(34) pp 20487–20495 (1989) "Activity and deletion analysis of recombinant human cathespin L expressed in *Escherichia coli*".
Tao et al *Arch. of Biochem. and Biophysics,* 311(1) pp 19–27 (1994) "The proregion of cathespin L is required for proper folding, stability, and ER exit."
McQueney et al., *J. Biol. Chem.* 272(21) pp 13955–13960 (1997) "Autocatalytic activation of human cathespin K."
Brömme et al. *J. Biol. Chem.* 271(4) pp 2126–2132 (1996) "Human cathepsin O2, a matrix protein–degrading cysteine protease expressed in osteoclasts."
Bossard et al. *J. Biol. Chem.* 271(21) pp 12517–12524 (1996) "Proteolytic activity of human osteoclast cathepsin K."
Drake et al. *J. Biol. Chem.* 271(21) pp 12511–12516 (1996) "Cathepsin K, but not cathepsins B, L, or S, is abundantly expressed in human osteoclasts."

Linnevers et al. *Protein Science* 6 pp 919–921 (1997) "Expression of human cathepsin K in *Pichia pastoris* and preliminary crystallographic studies of an inhibitor complex."
Vernet et al. *J. Biol. Chem.* 265(27) pp 16661–16666 (1990) "Secretion of functional papain precursor from insect cells."
Hasnain et al. *J. Biol. Chem.* 267(7) pp 4713–4721 (1992) "Characterization of recombinant rat cathepsin B and non-glycosylated mutants expressed in yeast."
Brömme et al. *J. Biol. Chem.* 268(7) pp 4832–4838 (1993) "Functional expression of human cathepsin S in *Saccharomyces cerevisiae*."
Vernet et al. *J. Biol. Chem.* 270(18) pp 10838–10846 (1995) "Processing of the papain precursor."
Brömme et al. *Biol. Chem. Hoppe–Seyler* 376 pp 611–615 (1995) "The baculovirus cysteine protease has a cathepsin B–like S2–subsite specificity."
Drake, F. et al., "Identification of a Novel Osteoclast–Selective Human Cysteine Proteinase," *Journal of Bone and Mineral Research,* 9(Supp. 1):S177 (Abstract A110) (Aug. 1994).
Li, YP et al., "Cloning and Characterization of a Novel Cathepsin from Human Osteoclasts," *34th Annual Meeting: The American Society for Cell Biology,* p. 335a (Abstract 1945) (Dec. 1994) San Francisco, California.
Tezuka, K., et al., "Molecular Cloning of a Possible Cysteine Proteinase Predominantly Expressed In Osteoclasts," *J. Biol. Chem.,* 269(2):1106–1109 (1994).
Delaisse, J.M., et al., "Inhibition of Bone Resorption in Culture by Inhibitors of Thiol Proteinases," *The Biochemical Society,* 192:365–368 (1980).
Everts, V., et al., Effects of the Proteinase Inhibitors Leupeptin and E–64 On Osteoclast Bone Resorption, *Calcif. Tissue Int.,* 43:172–178 (1988).
Sasaki, T., et al., "Cystein–Proteinase Localization in Osteoclasts: An Immunocytochemical Study," *Cell Tissue Res.,* 271:177–179 (1993).
Delaisse, J.M., "Collagenolytic Cysteine Proteinases of Bone Tissue," *The Biochemical Society,* 279:167–174 (1991).
Eeckhout, Y., et al., "Possible Role and Mechanism of Action of Dissolved Calcium in the Degradation of Bone Collagen by Lysosomal Cathepsins and Collagenase," *Biochem. J.,* 272:529–532 (1990).
Van Noorden, C.J.F., et al., "Cysteine Proteinase Activity in Arthritic Rat Knee Joints and the Effects of a Selective Systemic Inhibitor, Z–Phe–AlaCh$_2$F," *The Journal of Rheumatology,* 15(10):1525–1535 (1988).

(List continued on next page.)

*Primary Examiner*—Rebecca E. Prouty
*Assistant Examiner*—Richard Hutson
(74) *Attorney, Agent, or Firm*—David J. Brezner; Dorsey & Whitney LLP

(57) ABSTRACT

The invention relates to cathepsin O2 proteins, nucleic acids, and antibodies.

3 Claims, 14 Drawing Sheets

OTHER PUBLICATIONS

Delaisse, J.M., et al., "Mechanism of Mineral Solubilization and Matrix Degradation in Osteoclastic Bone Resorption," *Biology and Physiology of the Osteoclast,* Ch. 14:289–314 (1991).

Shi, G.P., et al., "Molecular Cloning of Human Cathepsin, a Novel Endoproteinase and Homologue of Rabbit OC2," *FEBS Letters,* 357:129–134 (1995).

Inaoka, T., et al., "Molecular Cloning of Human cDNA For Cathepsin K: Novel Cysteine Proteinase Predominantly Expressed in Bone," *Biochem. Biophys. Res. Comm.,* 206(1):89–96 (1995).

Wiederanders, B., et al., "Phylogenetic Conservation of Cysteine Proteinases: Cloning and Expression of a cDNA Coding for Human Cathepsin S," *J. Biol. Chem.,* 267:13708–13713 (1992).

Tsukuba, T., et al., "Isolation and Characterization of Recombinant Human Cathepsin E Expressed in Chinese Hamster Ovary Cells," *J. Biol. Chem.,* 268:7276–7282 (1993).

* cited by examiner

```
GCGCACTCAC AGTCGCAACC TTTCCCCTTC CTGACTTCCC GCTGACTTCC GCAATCCCGA    60
TGGAATAAAT CTAGCACCCC TGATGGTGTG CCCACACTTT GCTGCCGAAA CGAAGCCAGA   120
CAACAGATTT CCATCAGCAG C ATG TGG GGG CTC AAG GTT CTG CTA CCT        171
              Met Trp Gly Leu Lys Val Leu Leu Leu Pro
               1                                  10

GTG GTG AGC TTT GCT CTG TAC CCT GAG GAG ATA CTG GAC ACC CAC TGG   219
Val Val Ser Phe Ala Leu Tyr Pro Glu Glu Ile Leu Asp Thr His Trp
                    15                                       25

GAG CTA TGG AAG AAG ACC CAC AGG AAG CAA TAT AAC AAC AAG GTG GAT   267
Glu Leu Trp Lys Lys Thr His Arg Lys Gln Tyr Asn Asn Lys Val Asp
        30                                  35                40

GAA ATC TCT CGG CGT TTA ATT TGG GAA AAA AAC CTG AAG TAT ATT TCC   315
Glu Ile Ser Arg Arg Leu Ile Trp Glu Lys Asn Leu Lys Tyr Ile Ser
45                                  50                      55

ATC CAT AAC CTT GAG GCT TCT CTT GGT GTC CAT ACA TAT GAA CTG GCT   363
Ile His Asn Leu Glu Ala Ser Leu Gly Val His Thr Tyr Glu Leu Ala
        60                              65                      70

ATG AAC CAC CTG GGG GAC ATG ACC AGT GAA GAG GTG GTT CAG AAG ATG   411
Met Asn His Leu Gly Asp Met Thr Ser Glu Glu Val Val Gln Lys Met
        75                          80                      85                 90

ACT GGA CTC AAA GTA CCC CTG TCT CAT TCC CGC AGT AAT GAC ACC CTT   459
Thr Gly Leu Lys Val Pro Leu Ser His Ser Arg Ser Asn Asp Thr Leu
                        95                      100                     105

TAT ATC CCA GAA TGG GAA GGT AGA GCC CCA GAC TCT GTC GAC TAT CGA   507
Tyr Ile Pro Glu Trp Glu Gly Arg Ala Pro Asp Ser Val Asp Tyr Arg
110                                 115                     120
```

FIG._1A

```
AAG AAA GGA TAT GTT ACT CCT GTC AAA AAT CAG GGT CAG TGT GGT TCC    555
Lys Lys Gly Tyr Val Thr Pro Val Lys Asn Gln Gly Gln Cys Gly Ser
        125                 130                 135

TGT TGG GCT TTT AGC TCT GTG GGT GCC CTG GAG GGC CAA CTC AAG AAG    603
Cys Trp Ala Phe Ser Ser Val Gly Ala Leu Glu Gly Gln Leu Lys Lys
    140                 145                 150

AAA ACT GGC AAA CTC TTA AAT CTG AGT CCC CAG AAC CTA GTG GAT TGT    651
Lys Thr Gly Lys Leu Leu Asn Leu Ser Pro Gln Asn Leu Val Asp Cys
155                 160                 165                 170

GTG TCT GAG AAT GAT GGC TGT GGA GGG GGC TAC ATG ACC AAT GCC TTC    699
Val Ser Glu Asn Asp Gly Cys Gly Gly Gly Tyr Met Thr Asn Ala Phe
                175                 180                 185

CAA TAT GTG CAG AAG AAC CGG GGT ATT GAC TCT GAA GAT GCC TAC CCA    747
Gln Tyr Val Gln Lys Asn Arg Gly Ile Asp Ser Glu Asp Ala Tyr Pro
            190                 195                 200

TAT GTG GGA CAG GAA GAG AGT TGT ATG TAC AAC CCA ACA GGC AAG GCA    795
Tyr Val Gly Gln Glu Glu Ser Cys Met Tyr Asn Pro Thr Gly Lys Ala
        205                 210                 215

GCT AAA TGC AGA GGG TAC AGA GAG ATC CCC GAG GGG AAT GAG AAA GCC    843
Ala Lys Cys Arg Gly Tyr Arg Glu Ile Pro Glu Gly Asn Glu Lys Ala
    220                 225                 230

CTG AAG AGG GCA GTG GCC CGA GTG GGA CCT GTC TCT GTG GCC ATT GAT    891
Leu Lys Arg Ala Val Ala Arg Val Gly Pro Val Ser Val Ala Ile Asp
235                 240                 245                 250

GCA AGC CTG ACC TCC TTC CAG TTT TAC AGC AAA GGT GTG TAT TAT GAT    939
Ala Ser Leu Thr Ser Phe Gln Phe Tyr Ser Lys Gly Val Tyr Tyr Asp
                255                 260                 265
```

FIG._1B

```
GAA AGC TGC AAT AGC GAT AAT CTG AAC CAT GCG GTT TTG GCA GTG GGA    987
Glu Ser Cys Asn Ser Asp Asn Leu Asn His Ala Val Leu Ala Val Gly
                270                 275                 280

TAT GGA ATC CAG AAG GGA AAC AAG CAC TGG ATA ATT AAA AAC AGC TGG   1035
Tyr Gly Ile Gln Lys Gly Asn Lys His Trp Ile Ile Lys Asn Ser Trp
        285                 290                 295

GGA GAA AAC TGG GGA AAC AAA GGA TAT ATC CTC ATG GCT CGA AAT AAG   1083
Gly Glu Asn Trp Gly Asn Lys Gly Tyr Ile Leu Met Ala Arg Asn Lys
300                 305                 310

AAC AAC GCC TGT GGC ATT GCC AAC CTG GCC AGC TTC CCC AAG ATG       1128
Asn Asn Ala Cys Gly Ile Ala Asn Leu Ala Ser Phe Pro Lys Met
315                 320                 325

TGACTCCAGC CAGCCAAATC CATCCTGCTC TTCCATTTCT TCCACGATGG TGCAGTGTAA  1188

CGATGCACTT TGGAAGGGAG TTGGTGTGCT ATTTTTGAAG CAGATGTGGT GATACTGAGA  1248

TTGTCTGTTC AGTTCCCCCA TTTGTTTGTG CTTCAAATGA TCCTTCCTAC TTTGCTTCTC  1308

TCCACCCATG ACCTTTTTCA CAGGACTTTC CCTGACAGCT GTGTACTCTT            1368

AGGCTAAGAG ATGTGACTAC AGCCTGCCCC TGACTGTGTT GTCCCAGGGC TGATGCTGTA  1428

CAGGTACAGG CTGGAGATTT TCACATAGGT TAGATTCTCA TTCACGGGAC CCGG       1482
```

*FIG._1C*

```
HCat0   MWGLKVLL-- ---L--PVVS FA-LYPEEIL DTHWEL-WKK TH-RKQYNNK VDEISRRL   48
OC2     MWGLKVLL-- ---L--PVVS FA-LHPEEIL DTQWEL-WKK TY-SKQYNSK VDEISRRL   48
HCatS   MKRLVCVL-- ---LVC-SSA VAQLHKDPTL DHHWHL-WKK TY-GKQYKEK NEEAVRRL   50
HCatL   MNPTLILA-- ---AFCLGIA SATLTFDHSL EAQWTK-WKA MHNRL-YGM- NEEGWRRA   50
HCatH   MWATLPLLCA GAWLLCVPVC GAAELCVNSL EKFHFKSWMS KHRKT-YST- -EEYHHRL   55
HCatB   MWQLWASLC- -----CLIVL ANA------- ---------- -RSRPSFHPV S-DEL-VN   31
cons.   M......l.. ..l....... .a........l .........w.. .........y... ..E...r..

HCat0   -IWEKNLKYI SIHNLEASLG VHTYLLAMNH LGDMTSEEVV QKMTGLKVPL SHSRSND   104
OC2     -IWEKNLKHI SIHNLEASLG VHTYELAMNH LGDMTSEEVV QKMTGLKVPP SRSHSND   104
HCatS   -IWEKNLKFV MLHNLEHSMG MHSYDLGMNH LGDMTSEEVM SLMSSLRVP- -SQWQRN   104
HCatL   -VWEKNMKMI ELHNQEYREG KHSFTMAMNA FGDMTSEEFR QVMNGFQ--- NRKPRKG   103
HCatH   QTFASNWRKI NAHN----NG NHTFKMALNQ FSDMSFAEIK HKY-LWSEPQ NCSATK-   106
HCatB   YVNKRNTTWQ AGHNFYNVDM SYLKRLCGTF LGGPKPPQRV MFTEDLK--- -------    79
cons.   .......N.. ..HN......g .h........n ...m...e.. .........p.. .........

HCat0   TLYIPEWEGR APDSVDYRKK G----YVTPV KNQGQCGSCW AFSSVGALEG QLKKKTG   157
OC2     TLYIPDWEGR TPDSIDYRKK G----YVTPV KNQGQCGSCW AFSSVGALEG QLKKKTG   157
HCatS   ITYKSNPNRI LPDSVDWREK G----CVTEV KYQGSCGACW AFSAVGALEA QLKLKTG   157
HCatL   KVFQEPLFYE APRSVDWREK G----YVTPV KNQGQCGSCW AFSATGALEG QMFRKTG   156
HCatH   SNYLRG-TGP YPPSVDWRKK GN---FVSPV KNQGACGSCW TFSTTGALES AIAIATG   159
HCatB   LPASFDAREQ WPQCPTIKEI RDQGSCGSCW AFGAVEAISD RICIHTN         126
cons.   .........P.S.DwRek ....v..v k.QG.CGsCW aFs..gAle. .......g HCat0   KLLNL--SPQ NLVDCVSE-- -NDGCGGGYM TNAFQYVQKN RGIDSEDAY- ------P   202
OC2     KLLNL--SPQ NLVDCVSE-- -NYGCGGGYM TNAFQYVQRN RGIDSEDAY- ------P   202
HCatS   KLVSL--SAQ NLVDCSTEKY GNKGCNGGFM TTAFQYIIDN KGIDSDASY- ------P   205
HCatL   RLISL--SEQ NLVDCSGPQ- GNEGCNGGLM DYAFQYVQDN GGLDSEESY- ------P   203
HCatH   KMLSL--AEQ QLVDCA-QDF NNYGCQGGLP SQAFEYILYN KGIMGEDTY- ------P   206
HCatB   AHVSVEVSAE DLLTCCGSMC GD-GCNGGYP AEAWNF-WTR KGLVSGGLYE SHVGCRP   181
cons.   ....l..s.q .LvdC..... .n.GC.GG.. ..A..y...n .G..s...Y. ......P

FIG._2A
```

```
HCat0   Y------- -------V GQEESCM--- ---YNPTGKA AKCRGYREIP EGN-EKA     234
OC2     Y------- -------V GQDESCM--- ---YNPTGKA AKCRGYREIP EGN-EKA     234
HCatS   Y------- -------K AMDQKCQ--- ---YDSKYRA ATCSKYTELP YGR-EDV     237
HCatL   Y------- -------E ATEESCK--- ---YNPKYSV ANDTGFVDIP K-Q-EKA     234
HCatH   Y------- -------Q GKDGYCK--- ---FQPGKAI GFVKDVANIT IYD-EEA     239
HCatB   YSIPPCEHHV NGSRPPCTGE GDTPKCSKIC EPGYSPTYKQ DKHYGYNSYS VSNSEKD   238
cons.   .Y......  ........ ......C... ...y.p.... .......... .....E..

HCat0   LKRAVARVGP VSVAIDASLT SFQFYSKGVY YDESC--NSD NLN-HAVLAV GYG----   284
OC2     LKRAVARVGP VSVAIDASLT SFQFYSKGVY YDENC--SSD NVN-HAVLAV GYG----   284
HCatS   LKEAVANKGP VSVGVDARHP SFFLYRSGVY Y-EPS--CTQ NVN-HGVLVV GYG----   286
HCatL   LMKAVATVGP ISVAIDAGHE SFLFYKEGIY FEPDC--SSE DMD-HGVLVV GYGFEST   288
HCatH   MVEAVALYNP VSFAFEVTQD -FMMYRTGIY SSTSCHKTPD KVN-HAVLAV GYG----   289
HCatB   IMAEIYKNGP VEGAFSV-YS DFLLYKSGVY Q-----HVTGE MMGGHAIRIL GWGVE--  288
cons.   ...av a..gP vs.a..... .F..Y..G.Y ..........  ....H.vl.v GyG....
                      *                                      *

HCat0   IQKGNKHWII KNSWGENWGN KGYILMARNK NNACGIANLA SF--PK--- ---M     329
OC2     IQKGNKHWII KNSWGESWGN KGYILMARNK NNACGIANLA SF--PK--- ---M     329
HCatS   DLNGKEYWLV KNSWGHNFGE EGYIRMARNK GNHCGIASFP SY--PE--- ---I     331
HCatL   ESDNNKYWLV KNSWGEEWGM GGYVKMAKDR RNHCGIASAA SY--PT--- ---V     333
HCatH   EKNGIPYWIV KNSWGPQWGM NGYFLIERGK -NMCGLAACA SYPIPL--- ---V     335
HCatB   --NGTPYWLV ANSWNTDWGD NGFFKILGGQ -DHCGIESEV VAGIPRTDQY WEKI     339
cons.   ....g.... .W... kNSWg. .wG..   .Gy.......  .n.CGia...  ....P....
```

FIG._2B

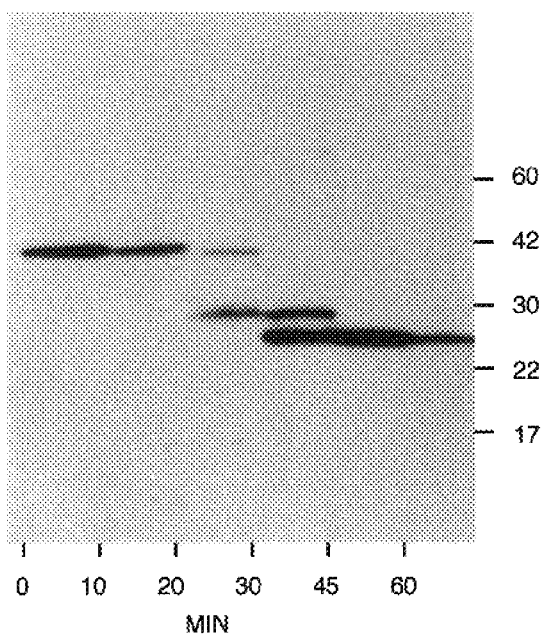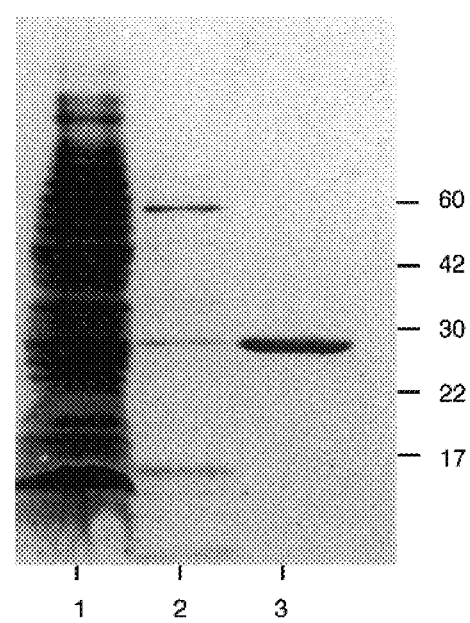
FIG._3    FIG._4

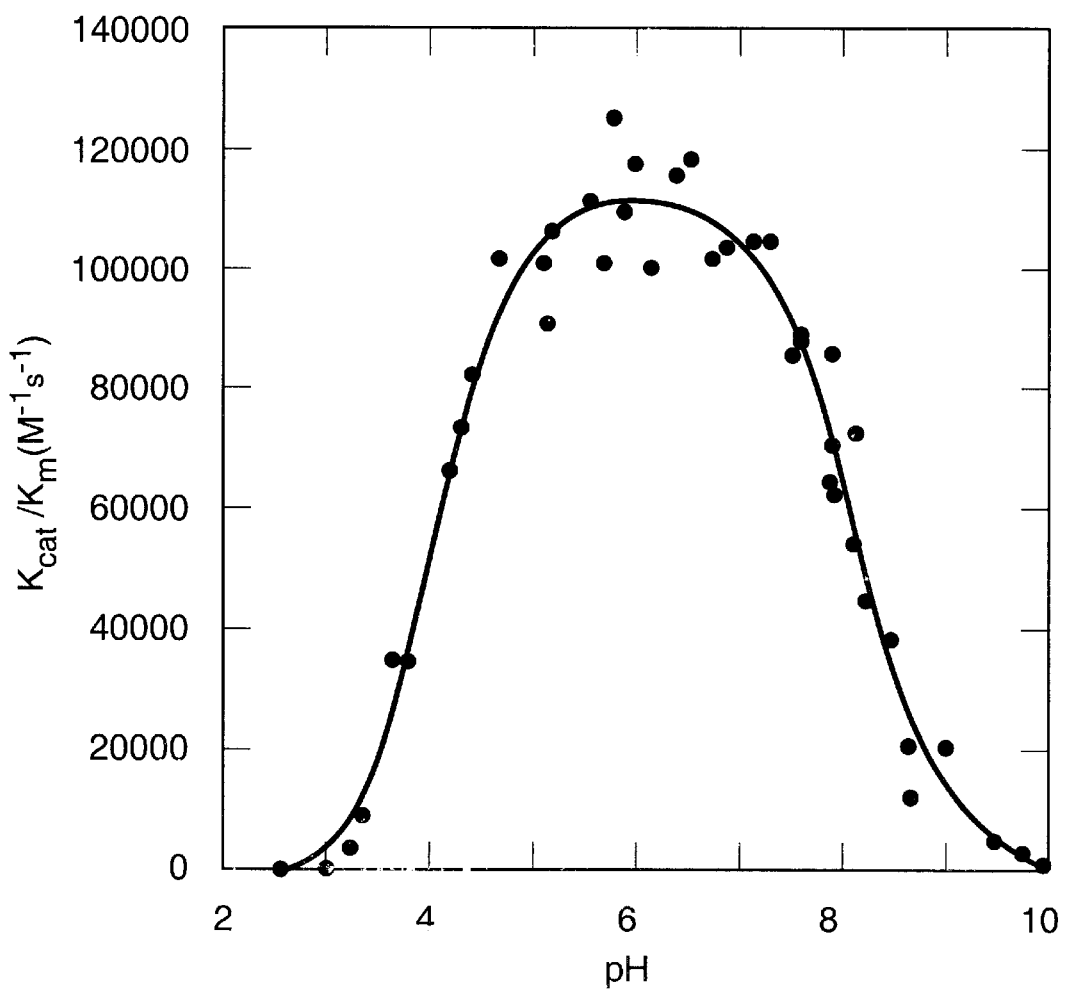
FIG._5

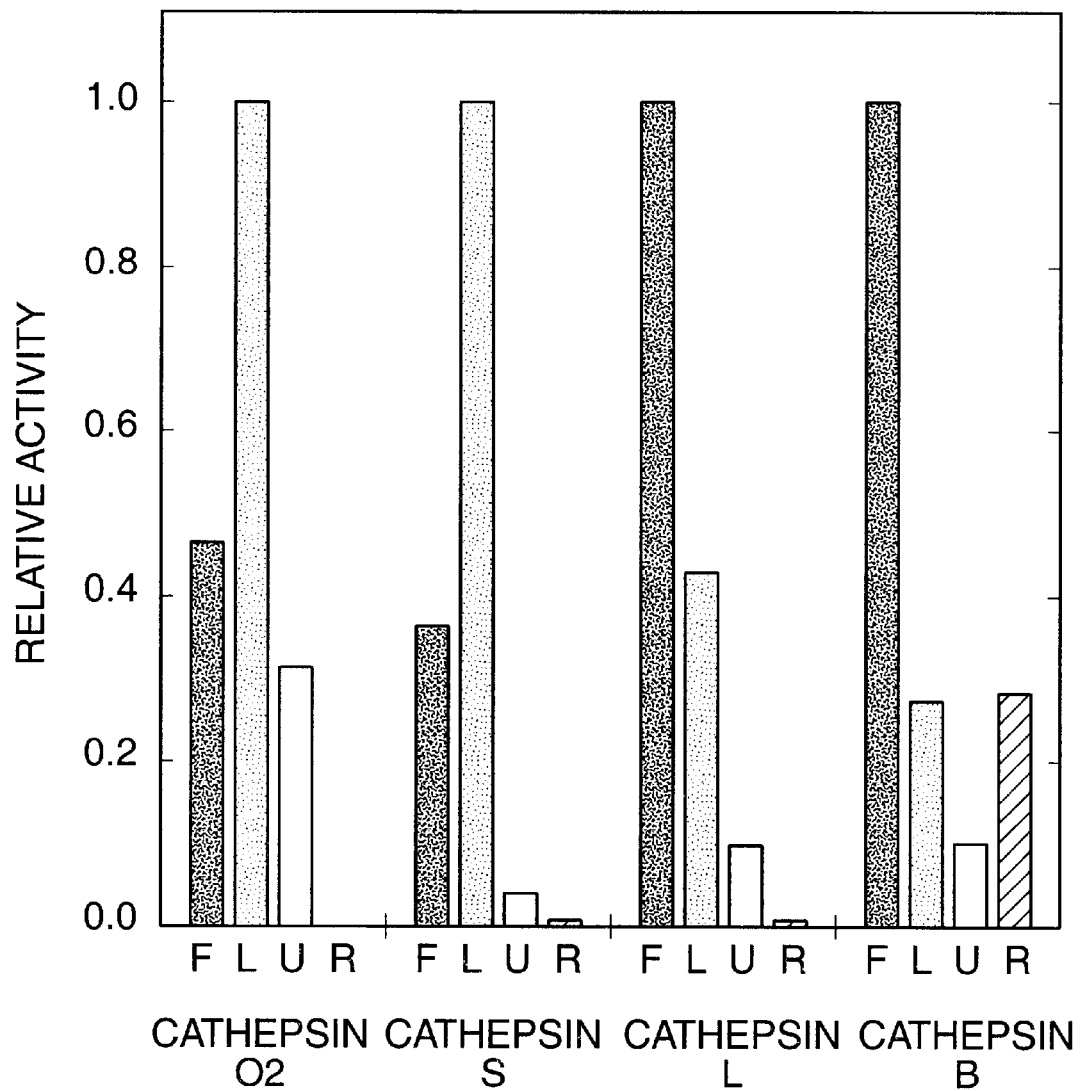
FIG._6

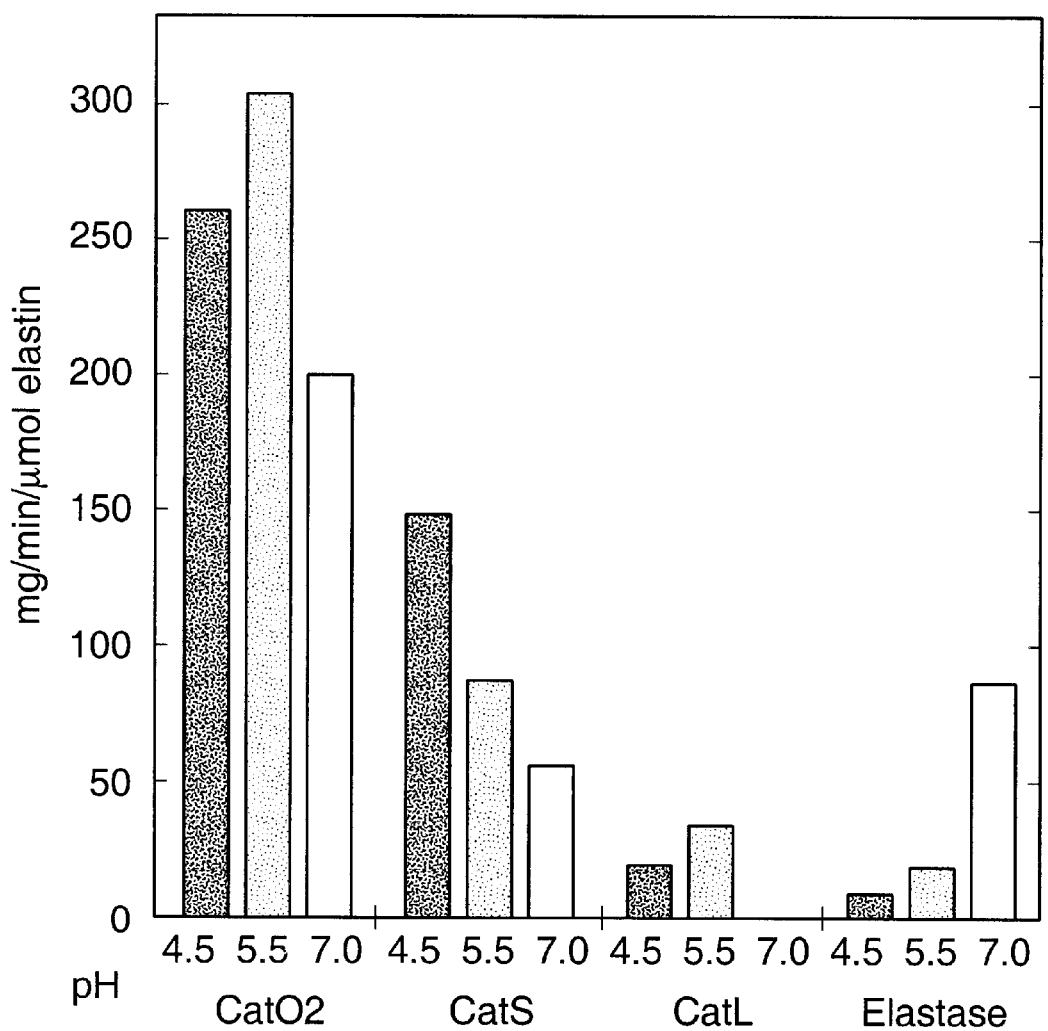
FIG._7

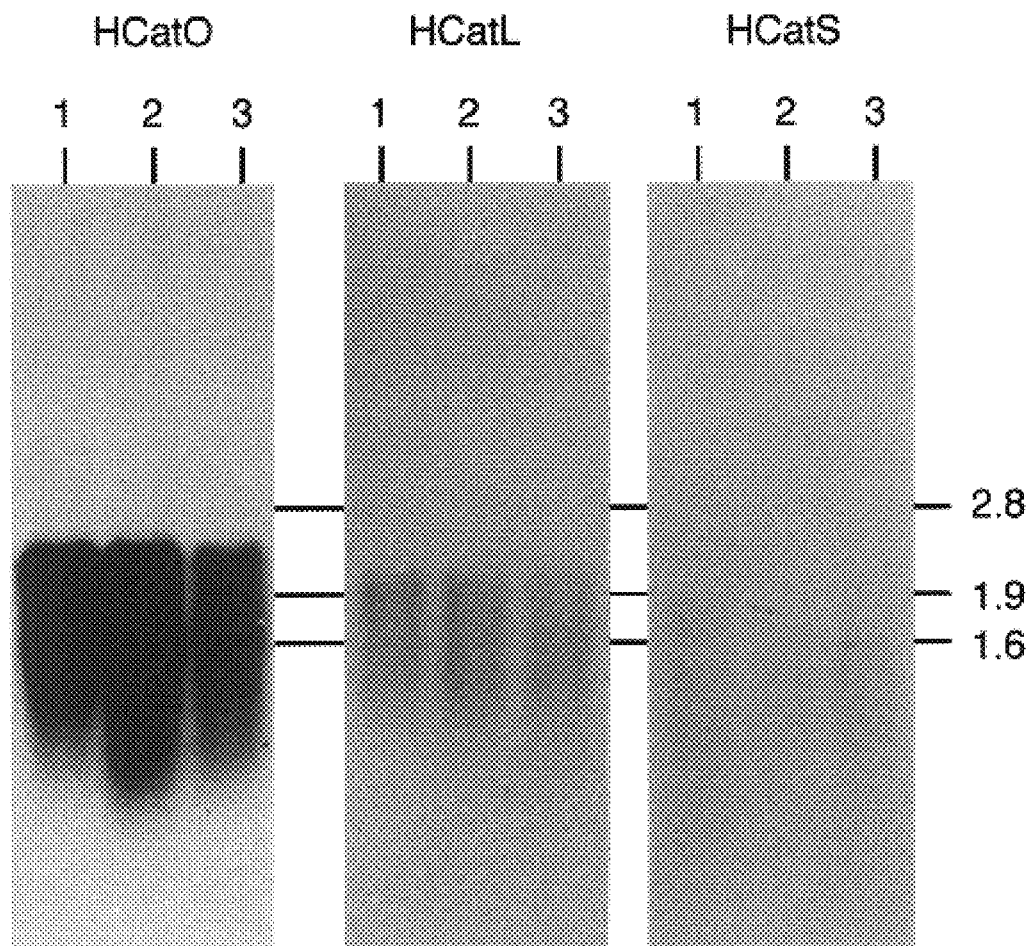
FIG._8

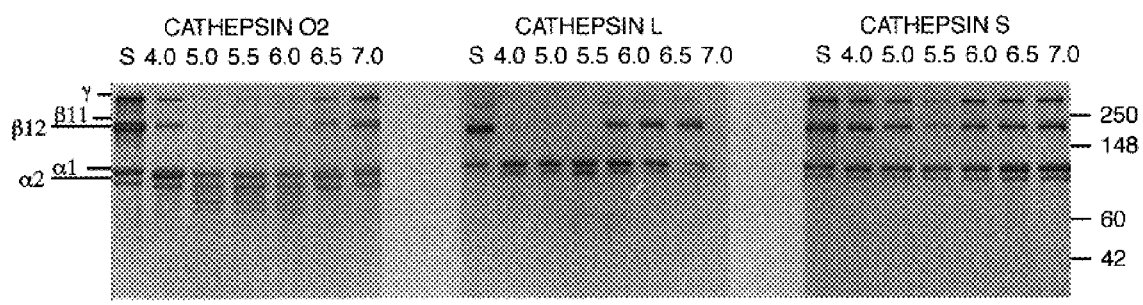
FIG._9A
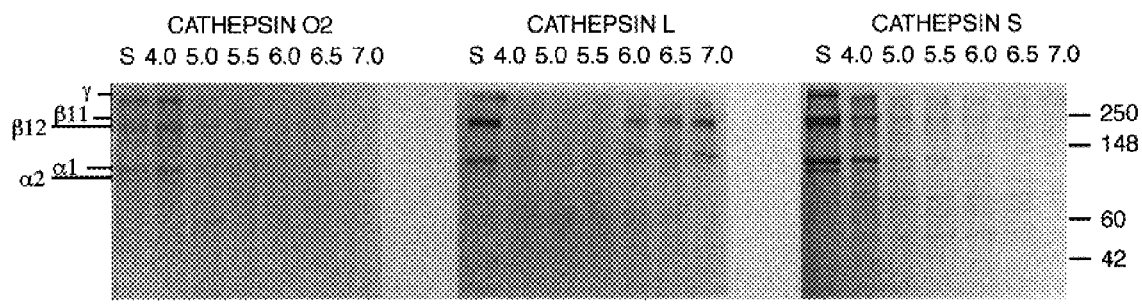
FIG._9B

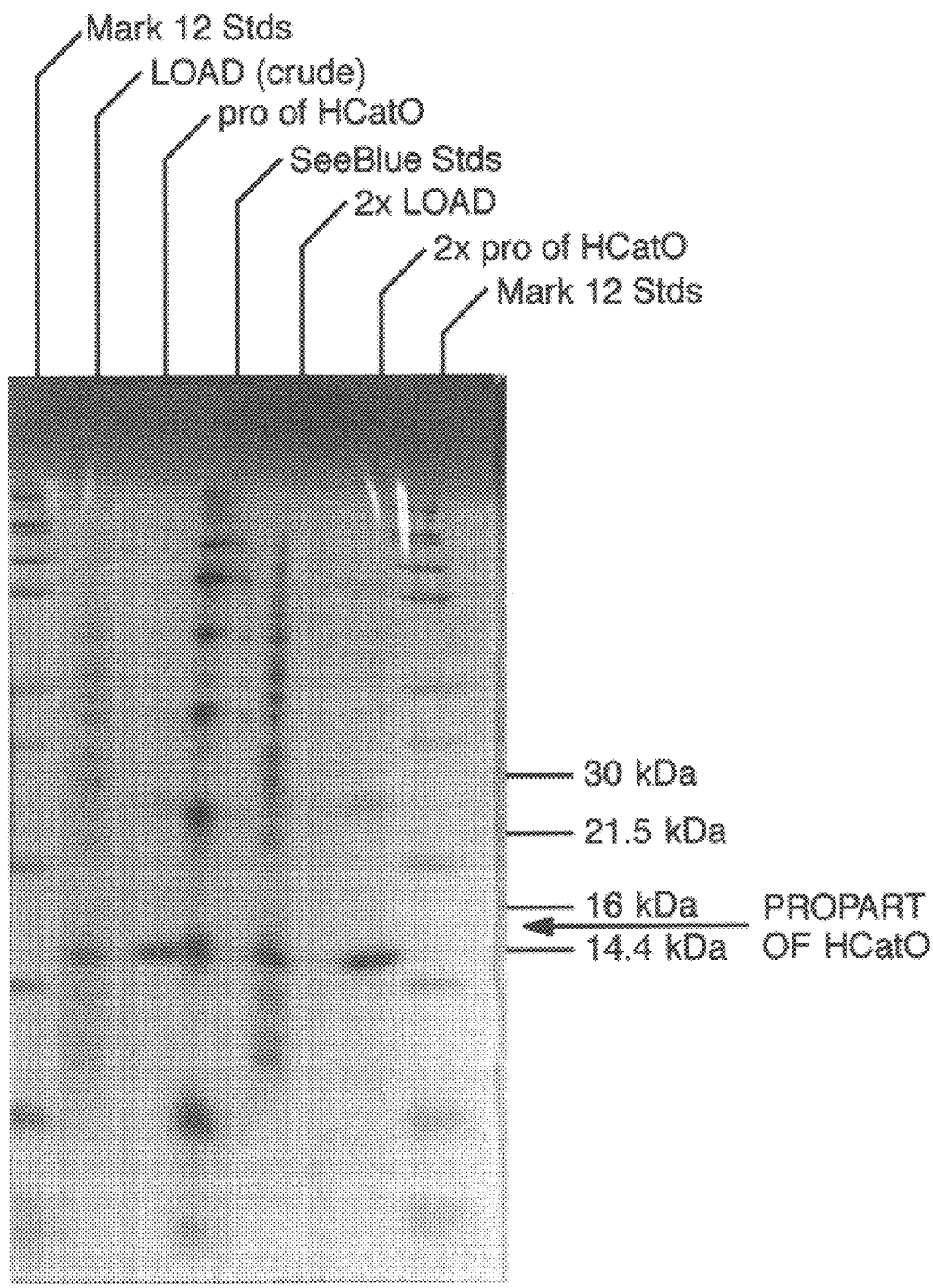
FIG._10

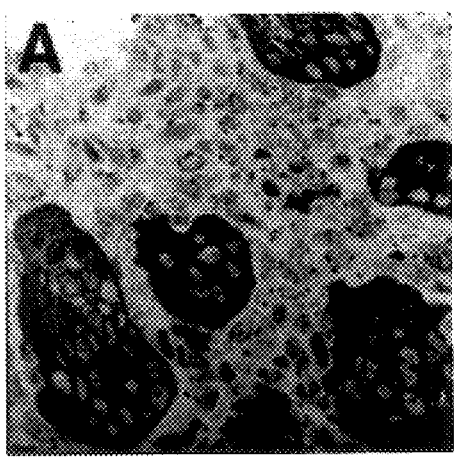
FIG._11A
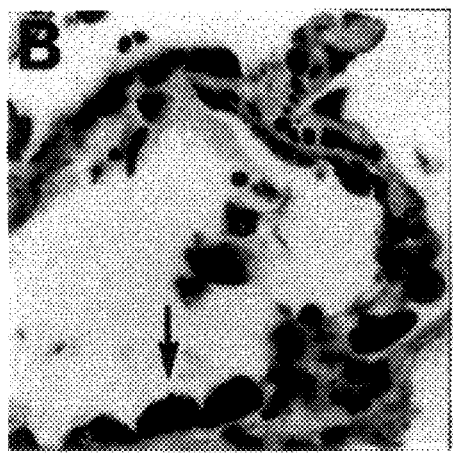
FIG._11B
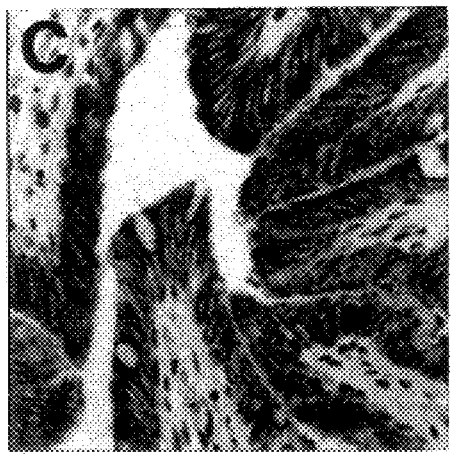
FIG._11C
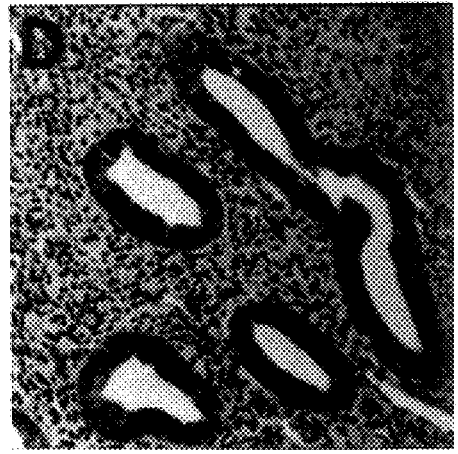
FIG._11D
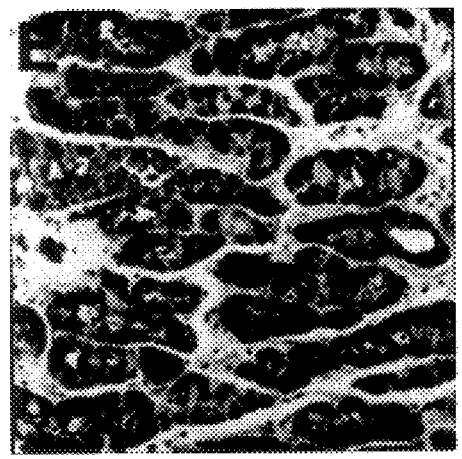
FIG._11E
FIG._11F

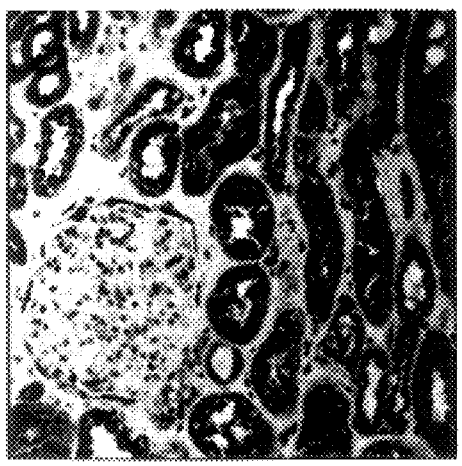
FIG._11G
FIG._11H
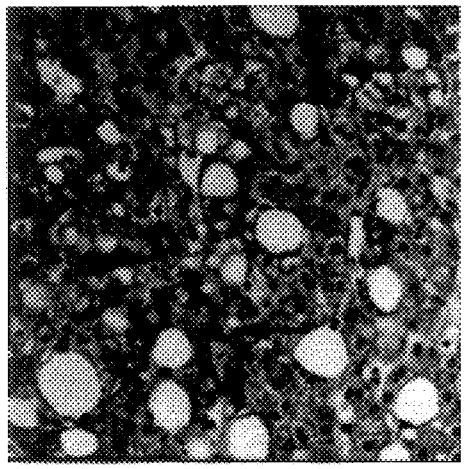
FIG._11I
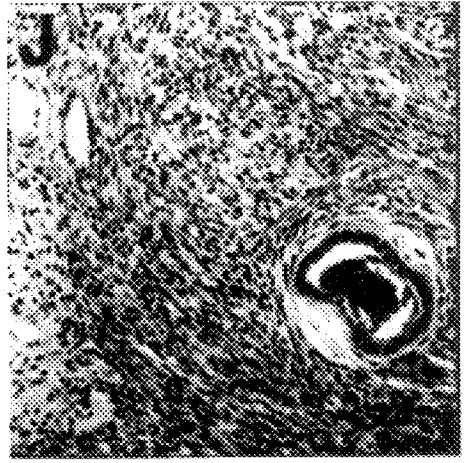
FIG._11J
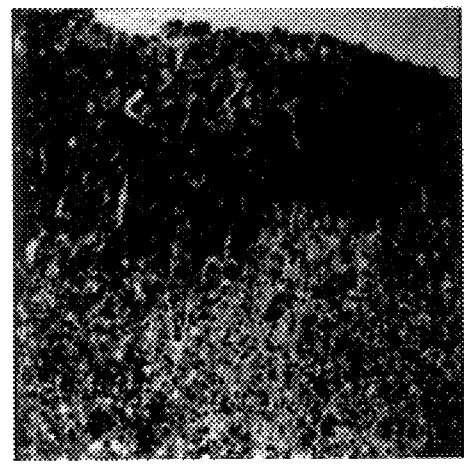
FIG._11K
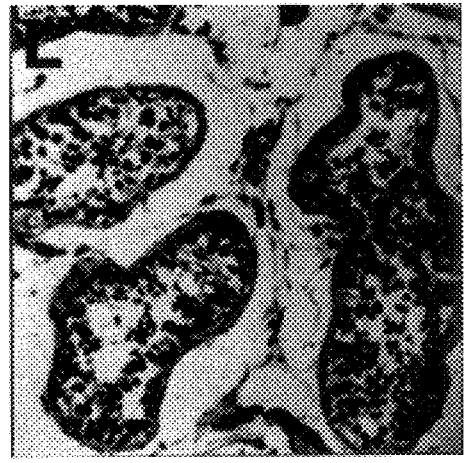
FIG._11L

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1482 base pairs
      (B) TYPE: nucleic acid

```
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 142..1128

(xi) SEQUENCE DESCRIPTION: SEQ ID NO:1:

GCGCACTCAC AGTCGCAACC TTTCCCCTTC CTGACTTCCC GCTGACTTCC GCAATCCCGA         60

TGGAATAAAT CTAGCACCCC TGATGGTGTG CCCACACTTT GCTGCCGAAA CGAAGCCAGA        120

CAACAGATTT CCATCAGCAG C ATG TGG GGG CTC AAG GTT CTG CTG CTA CCT         171
                       Met Trp Gly Leu Lys Val Leu Leu Leu Pro
                         1               5                  10

GTG GTG AGC TTT GCT CTG TAC CCT GAG GAG ATA CTG GAC ACC CAC TGG         219
Val Val Ser Phe Ala Leu Tyr Pro Glu Glu Ile Leu Asp Thr His Trp
             15                  20                  25

GAG CTA TGG AAG AAG ACC CAC AGG AAG CAA TAT AAC AAC AAG GTG GAT         267
Glu Leu Trp Lys Lys Thr His Arg Lys Gln Tyr Asn Asn Lys Val Asp
         30                  35                  40

GAA ATC TCT CGG CGT TTA ATT TGG GAA AAA AAC CTG AAG TAT ATT TCC         315
Glu Ile Ser Arg Arg Leu Ile Trp Glu Lys Asn Leu Lys Tyr Ile Ser
     45                  50                  55

ATC CAT AAC CTT GAG GCT TCT CTT GGT GTC CAT ACA TAT GAA CTG GCT         363
Ile His Asn Leu Glu Ala Ser Leu Gly Val His Thr Tyr Glu Leu Ala
 60                  65                  70

ATG AAC CAC CTG GGG GAC ATG ACC AGT GAA GAG GTG GTT CAG AAG ATG         411
Met Asn His Leu Gly Asp Met Thr Ser Glu Glu Val Val Gln Lys Met
 75                  80                  85                  90

ACT GGA CTC AAA GTA CCC CTG TCT CAT TCC CGC AGT AAT GAC ACC CTT         459
Thr Gly Leu Lys Val Pro Leu Ser His Ser Arg Ser Asn Asp Thr Leu
                 95                 100                 105

TAT ATC CCA GAA TGG GAA GGT AGA GCC CCA GAC TCT GTC GAC TAT CGA         507
Tyr Ile Pro Glu Trp Glu Gly Arg Ala Pro Asp Ser Val Asp Tyr Arg
             110                 115                 120

AAG AAA GGA TAT GTT ACT CCT GTC AAA AAT CAG GGT CAG TGT GGT TCC         555
Lys Lys Gly Tyr Val Thr Pro Val Lys Asn Gln Gly Gln Cys Gly Ser
         125                 130                 135

TGT TGG GCT TTT AGC TCT GTG GGT GCC CTG GAG GGC CAA CTC AAG AAG         603
Cys Trp Ala Phe Ser Ser Val Gly Ala Leu Glu Gly Gln Leu Lys Lys
     140                 145                 150

AAA ACT GGC AAA CTC TTA AAT CTG AGT CCC CAG AAC CTA GTG GAT TGT         651
Lys Thr Gly Lys Leu Leu Asn Leu Ser Pro Gln Asn Leu Val Asp Cys
155                 160                 165                 170

GTG TCT GAG AAT GAT GGC TGT GGA GGG GGC TAC ATG ACC AAT GCC TTC         699
Val Ser Glu Asn Asp Gly Cys Gly Gly Gly Tyr Met Thr Asn Ala Phe
                 175                 180                 185

CAA TAT GTG CAG AAG AAC CGG GGT ATT GAC TCT GAA GAT GCC TAC CCA         747
Gln Tyr Val Gln Lys Asn Arg Gly Ile Asp Ser Glu Asp Ala Tyr Pro
             190                 195                 200

TAT GTG GGA CAG GAA GAG AGT TGT ATG TAC AAC CCA ACA GGC AAG GCA         795
Tyr Val Gly Gln Glu Glu Ser Cys Met Tyr Asn Pro Thr Gly Lys Ala
         205                 210                 215

GCT AAA TGC AGA GGG TAC AGA GAG ATC CCC GAG GGG AAT GAG AAA GCC         843
Ala Lys Cys Arg Gly Tyr Arg Glu Ile Pro Glu Gly Asn Glu Lys Ala
     220                 225                 230

CTG AAG AGG GCA GTG GCC CGA GTG GGA CCT GTC TCT GTG GCC ATT GAT         891
Leu Lys Arg Ala Val Ala Arg Val Gly Pro Val Ser Val Ala Ile Asp
235                 240                 245                 250
```

```
GCA AGC CTG ACC TCC TTC CAG TTT TAC AGC AAA GGT GTG TAT TAT GAT    939
Ala Ser Leu Thr Ser Phe Gln Phe Tyr Ser Lys Gly Val Tyr Tyr Asp
                255                 260                 265

GAA AGC TGC AAT AGC GAT AAT CTG AAC CAT GCG GTT TTG GCA GTG GGA    987
Glu Ser Cys Asn Ser Asp Asn Leu Asn His Ala Val Leu Ala Val Gly
                270                 275                 280

TAT GGA ATC CAG AAG GGA AAC AAG CAC TGG ATA ATT AAA AAC AGC TGG   1035
Tyr Gly Ile Gln Lys Gly Asn Lys His Trp Ile Ile Lys Asn Ser Trp
                285                 290                 295

GGA GAA AAC TGG GGA AAC AAA GGA TAT ATC CTC ATG GCT CGA AAT AAG   1083
Gly Glu Asn Trp Gly Asn Lys Gly Tyr Ile Leu Met Ala Arg Asn Lys
        300                 305                 310

AAC AAC GCC TGT GGC ATT GCC AAC CTG GCC AGC TTC CCC AAG ATG       1128
Asn Asn Ala Cys Gly Ile Ala Asn Leu Ala Ser Phe Pro Lys Met
315                 320                 325

TGACTCCAGC CAGCCAAATC CATCCTGCTC TTCCATTTCT TCCACGATGG TGCAGTGTAA 1188

CGATGCACTT TGGAAGGGAG TTGGTGTGCT ATTTTTGAAG CAGATGTGGT GATACTGAGA 1248

TTGTCTGTTC AGTTTCCCCA TTTGTTTGTG CTTCAAATGA TCCTTCCTAC TTTGCTTCTC 1308

TCCACCCATG ACCTTTTTCA CTGTGGCCAT CAGGACTTTC CCTGACAGCT GTGTACTCTT 1368

AGGCTAAGAG ATGTGACTAC AGCCTGCCCC TGACTGTGTT GTCCCAGGGC TGATGCTGTA 1428

CAGGTACAGG CTGGAGATTT TCACATAGGT TAGATTCTCA TTCACGGGAC CCGG       1482

(2) INFORMATION FOR SEQ ID NO:2:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:2:

Met Trp Gly Leu Lys Val Leu Leu Pro Val Val Ser Phe Ala Leu
  1               5                  10                  15

Tyr Pro Glu Glu Ile Leu Asp Thr His Trp Glu Leu Trp Lys Lys Thr
                 20                  25                  30

His Arg Lys Gln Tyr Asn Asn Lys Val Asp Glu Ile Ser Arg Arg Leu
             35                  40                  45

Ile Trp Glu Lys Asn Leu Lys Tyr Ile Ser Ile His Asn Leu Glu Ala
         50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
                 85                  90                  95

Leu Ser His Ser Arg Ser Asn Asp Thr Leu Tyr Ile Pro Glu Trp Glu
                100                 105                 110

Gly Arg Ala Pro Asp Ser Val Asp Tyr Arg Lys Lys Gly Tyr Val Thr
            115                 120                 125

Pro Val Lys Asn Gln Gly Gln Cys Gly Ser Cys Trp Ala Phe Ser Ser
        130                 135                 140

Val Gly Ala Leu Glu Gly Gln Leu Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
            180                 185                 190
```

```
Arg Gly Ile Asp Ser Glu Asp Ala Tyr Pro Tyr Val Gly Gln Glu Glu
            195                 200                 205
Ser Cys Met Tyr Asn Pro Thr Gly Lys Ala Ala Lys Cys Arg Gly Tyr
            210                 215                 220
Arg Glu Ile Pro Glu Gly Asn Glu Lys Ala Leu Lys Arg Ala Val Ala
225                 230                 235                 240
Arg Val Gly Pro Val Ser Val Ala Ile Asp Ala Ser Leu Thr Ser Phe
                245                 250                 255
Gln Phe Tyr Ser Lys Gly Val Tyr Tyr Asp Glu Ser Cys Asn Ser Asp
                260                 265                 270
Asn Leu Asn His Ala Val Leu Ala Val Gly Tyr Gly Ile Gln Lys Gly
            275                 280                 285
Asn Lys His Trp Ile Ile Lys Asn Ser Trp Gly Glu Asn Trp Gly Asn
            290                 295                 300
Lys Gly Tyr Ile Leu Met Ala Arg Asn Lys Asn Asn Ala Cys Gly Ile
305                 310                 315                 320
Ala Asn Leu Ala Ser Phe Pro Lys Met
                325

(2) INFORMATION FOR SEQ ID NO:3:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

Met Trp Gly Leu Lys Val Leu Leu Pro Val Val Ser Phe Ala Leu
1               5                   10                  15
His Pro Glu Glu Ile Leu Asp Thr Gln Trp Glu Leu Trp Lys Lys Thr
            20                  25                  30
Tyr Ser Lys Gln Tyr Asn Ser Lys Val Asp Glu Ile Ser Arg Arg Leu
            35                  40                  45
Ile Trp Glu Lys Asn Leu Lys His Ile Ser Ile His Asn Leu Glu Ala
        50                  55                  60
Ser Leu Gly Val His Thr Tyr Glu Leu Ala Met Asn His Leu Gly Asp
65                  70                  75                  80
Met Thr Ser Glu Glu Val Val Gln Lys Met Thr Gly Leu Lys Val Pro
                85                  90                  95
Pro Ser Arg Ser His Ser Asn Asp Thr Leu Tyr Ile Pro Asp Trp Glu
            100                 105                 110
Gly Arg Thr Pro Asp Ser Ile Asp Tyr Arg Lys Lys Gly Tyr Val Thr
            115                 120                 125
Pro Val Lys Asn Gln Gly Gln Cys Gly Ser Cys Trp Ala Phe Ser Ser
            130                 135                 140
Val Gly Ala Leu Glu Gly Gln Leu Lys Lys Lys Thr Gly Lys Leu Leu
145                 150                 155                 160
Asn Leu Ser Pro Gln Asn Leu Val Asp Cys Val Ser Glu Asn Tyr Gly
                165                 170                 175
Cys Gly Gly Gly Tyr Met Thr Asn Ala Phe Gln Tyr Val Gln Arg Asn
                180                 185                 190
Arg Gly Ile Asp Ser Glu Asp Ala Tyr Pro Tyr Val Gly Gln Asp Glu
            195                 200                 205
```

```
Ser Cys Met Tyr Asn Pro Thr Gly Lys Ala Ala Lys Cys Arg Gly Tyr
    210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Asn Cys Ser Ser Asp
            260                 265                 270

Asn Val Asn His Ala Val Leu Ala Val Gly Tyr Gly Ile Gln Lys Gly
            275                 280                 285

Asn Lys His Trp Ile Ile Lys Asn Ser Trp Gly Glu Ser Trp Gly Asn
        290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325

(2) INFORMATION FOR SEQ ID NO:4:

(i) SEQUENCE CHARACTERISTICS:
        (A) LENGTH: 331 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:4:

Met Lys Arg Leu Val Cys Val Leu Leu Val Cys Ser Ser Ala Val Ala
1               5                   10                  15

Gln Leu His Lys Asp Pro Thr Leu Asp His His Trp His Leu Trp Lys
            20                  25                  30

Lys Thr Tyr Gly Lys Gln Tyr Lys Glu Lys Asn Glu Glu Ala Val Arg
        35                  40                  45

Arg Leu Ile Trp Glu Lys Asn Leu Lys Phe Val Met Leu His Asn Leu
    50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Ser Gln Trp Gln Arg Asn Ile Thr Tyr Lys Ser Asn Pro Asn
            100                 105                 110

Arg Ile Leu Pro Asp Ser Val Asp Trp Arg Glu Lys Gly Cys Val Thr
        115                 120                 125

Glu Val Lys Tyr Gln Gly Ser Cys Gly Ala Cys Trp Ala Phe Ser Ala
    130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
        195                 200                 205

Met Asp Gln Lys Cys Gln Tyr Asp Ser Lys Tyr Arg Ala Ala Thr Cys
    210                 215                 220
```

```
Ser Lys Tyr Thr Glu Leu Pro Tyr Gly Arg Glu Val Asp Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Gly Tyr Gly Asp Leu
        275                 280                 285

Asn Gly Lys Glu Tyr Trp Leu Val Lys Asn Ser Trp Gly His Asn Phe
290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330

(2) INFORMATION FOR SEQ ID NO:5:

(i) SEQUENCE CHARACTERISTICS:
        (A) LENGTH: 333 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:5:

Met Asn Pro Thr Leu Ile Leu Ala Ala Phe Cys Leu Gly Ile Ala Ser
1               5                   10                  15

Ala Thr Leu Thr Phe Asp His Ser Leu Glu Ala Gln Trp Thr Lys Trp
                20                  25                  30

Lys Ala Met His Asn Arg Leu Tyr Gly Met Asn Glu Glu Gly Trp Arg
                35                  40                  45

Arg Ala Val Trp Glu Lys Asn Met Lys Met Ile Glu Leu His Asn Gln
50                  55                  60

Glu Tyr Arg Glu Gly Lys His Ser Phe Thr Met Ala Met Asn Ala Phe
65                  70                  75                  80

Gly Asp Met Thr Ser Glu Glu Phe Arg Gln Val Met Asn Gly Phe Gln
                85                  90                  95

Asn Arg Lys Pro Arg Lys Gly Lys Val Phe Gln Glu Pro Leu Phe Tyr
                100                 105                 110

Glu Ala Pro Arg Ser Val Asp Trp Arg Glu Lys Gly Tyr Val Thr Pro
            115                 120                 125

Val Lys Asn Gln Gly Gln Cys Gly Ser Cys Trp Ala Phe Ser Ala Thr
    130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
                165                 170                 175

Gly Cys Asn Gly Gly Leu Met Asp Tyr Ala Phe Gln Tyr Val Gln Asp
                180                 185                 190

Asn Gly Gly Leu Asp Ser Glu Glu Ser Tyr Pro Tyr Glu Ala Thr Glu
            195                 200                 205

Glu Ser Cys Lys Tyr Asn Pro Lys Tyr Ser Val Ala Asn Asp Thr Gly
        210                 215                 220

Phe Val Asp Ile Pro Lys Gln Glu Lys Ala Leu Met Lys Ala Val Ala
225                 230                 235                 240
```

```
Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Gly Tyr Gly Phe Glu Ser Thr
            275                 280                 285

Glu Ser Asp Asn Asn Lys Tyr Trp Leu Val Lys Asn Ser Trp Gly Glu
        290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330
```

(2) INFORMATION FOR SEQ ID NO:6:

(i) SEQUENCE CHARACTERISTICS:
        (A) LENGTH: 335 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:6:

```
Met Trp Ala Thr Leu Pro Leu Leu Cys Ala Gly Ala Trp Leu Leu Cys
1               5                   10                  15

Val Pro Val Cys Gly Ala Ala Glu Leu Cys Val Asn Ser Leu Glu Lys
                20                  25                  30

Phe His Phe Lys Ser Trp Met Ser Lys His Arg Lys Thr Tyr Ser Thr
            35                  40                  45

Glu Glu Tyr His His Arg Leu Gln Thr Phe Ala Ser Asn Trp Arg Lys
        50                  55                  60

Ile Asn Ala His Asn Asn Gly Asn His Thr Phe Lys Met Ala Leu Asn
65                  70                  75                  80

Gln Phe Ser Asp Met Ser Phe Ala Glu Ile Lys His Lys Tyr Leu Trp
                85                  90                  95

Ser Glu Pro Gln Asn Cys Ser Ala Thr Lys Ser Asn Tyr Leu Arg Gly
                100                 105                 110

Thr Gly Pro Tyr Pro Pro Ser Val Asp Trp Arg Lys Lys Gly Asn Phe
            115                 120                 125

Val Ser Pro Val Lys Asn Gln Gly Ala Cys Gly Ser Cys Trp Thr Phe
130                 135                 140

Ser Thr Thr Gly Ala Leu Glu Ser Ala Ile Ala Ile Ala Thr Gly Lys
145                 150                 155                 160

Met Leu Ser Leu Ala Glu Gln Gln Leu Val Asp Cys Ala Gln Asp Phe
                165                 170                 175

Asn Asn Tyr Gly Cys Gln Gly Gly Leu Pro Ser Gln Ala Phe Glu Tyr
            180                 185                 190

Ile Leu Tyr Asn Lys Gly Ile Met Gly Glu Asp Thr Tyr Pro Tyr Gln
            195                 200                 205

Gly Lys Asp Gly Tyr Cys Lys Phe Gln Pro Gly Lys Ala Ile Gly Phe
        210                 215                 220

Val Lys Asp Val Ala Asn Ile Thr Ile Tyr Asp Glu Glu Ala Met Val
225                 230                 235                 240

Glu Ala Val Ala Leu Tyr Asn Pro Val Ser Phe Ala Phe Glu Val Thr
                245                 250                 255
```

```
Gln Asp Phe Met Met Tyr Arg Thr Gly Ile Tyr Ser Ser Thr Ser Cys
            260                 265                 270

His Lys Thr Pro Asp Lys Val Asn His Ala Val Leu Ala Val Gly Tyr
            275                 280                 285

Gly Glu Lys Asn Gly Ile Pro Tyr Trp Ile Val Lys Asn Ser Trp Gly
            290                 295                 300

Pro Gln Trp Gly Met Asn Gly Tyr Phe Leu Ile Glu Arg Gly Lys Asn
305                 310                 315                 320

Met Cys Gly Leu Ala Ala Cys Ala Ser Tyr Pro Ile Pro Leu Val
                325                 330                 335

(2) INFORMATION FOR SEQ ID NO:7:

(i) SEQUENCE CHARACTERISTICS:
        (A) LENGTH: 339 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:7:

Met Trp Gln Leu Trp Ala Ser Leu Cys Cys Leu Leu Val Leu Ala Asn
1               5                   10                  15

Ala Arg Ser Arg Pro Ser Phe His Pro Val Ser Asp Glu Leu Val Asn
            20                  25                  30

Tyr Val Asn Lys Arg Asn Thr Thr Trp Gln Ala Gly His Asn Phe Tyr
            35                  40                  45

Asn Val Asp Met Ser Tyr Leu Lys Arg Leu Cys Gly Thr Phe Leu Gly
50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
            115                 120                 125

Val Ser Val Glu Val Ser Ala Glu Asp Leu Leu Thr Cys Cys Gly Ser
            130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
            195                 200                 205

Lys Ile Cys Glu Pro Gly Tyr Ser Pro Thr Tyr Lys Gln Asp Lys His
            210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270
```

```
Glu Met Met Gly Gly His Ala Ile Arg Ile Leu Gly Trp Gly Val Glu
            275                 280                 285

Asn Gly Thr Pro Tyr Trp Leu Val Ala Asn Ser Trp Asn Thr Asp Trp
            290                 295                 300

Gly Asp Asn Gly Phe Phe Lys Ile Leu Gly Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile
```

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:8:

```
GGATACGTTA CNCCNGT                                                17
```

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:9:

```
GCCATGAGRT ANCC                                                   14
```

(2) INFORMATION FOR SEQ ID NO:10:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:10:

```
Ala Pro Asp Ser Val Asp Tyr Arg Lys Lys Gly Tyr Val Thr Pro Val
1               5                   10                  15

Lys Asn
```

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:11:

```
CTGGATCCCT GTACCCTGAG GAGATACTG                                   29
```

(2) INFORMATION FOR SEQ ID NO:12:

(i) SEQUENCE CHARACTERISTICS:
       (A) LENGTH: 33 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO:12:

CTAAGCTTCT ATCTACCTTC CCATTCTGGG ATA                33

CATHESPIN O2 PROTEASE

This application is a continuation-in-part of U.S. Ser. No. 08/330,121, filed Oct. 27, 1994 now U.S. Pat. No. 5,736,357.

FIELD OF THE INVENTION

The invention relates to cathepsin O2 proteins, nucleic acids, and antibodies.

BACKGROUND OF THE INVENTION

The cathepsins belong to the papain superfamily of cysteine proteases. Cysteine or thiol proteases contain a cysteine residue, as well as a histidine and an asparagine, at the active site responsible for proteolysis. This superfamily also has a glutamine at the oxy-anion hole.

Recent work has implicated cysteine proteases in binding to DNA with putative transcription factor activity (Xu et al., J. Biol. Chem. 269(33):21177–21183 (1994)), and as a long term immunosuppressor (Hamajima et al., Parasite Immunology 16:261 (1994)).

To date, a number of cathepsins have been identified and sequenced from a number of animals. For example, cathepsin S has been cloned from rat (Petanceska et al., J. Biol. Chem. 267:26038–20643 (1992)), bovine (Wiederanders et al., FEBS Lett. 286:189–192 (1991)) and humans (Wideranders et al., J. Biol. Chem. 267:13708–13713 (1992); and Shi et al., J. Biol. Chem. 267:7258–7262 (1992)). Cathepsin L has been cloned from humans, rat, mouse and chicken (Gal et al. Biochem. J., 253:303–306 (1988); Ishidoh et al., FEBS Lett. 223:69–73 (1987); Joseph et al., J. Clin. Invest. 81:1621–1629 (1988); Ritonja et al., FEBS Lett. 283:329–331 (1991)). Cathepsin H has been cloned from human and rat (Fuchs et al., Biol. Chem. Hoppe-Seyler 369–375 (1988); Fuchs et al., Nucleic Acid Res. 17:9471 (1989); Whittier et al., Nucleic Acid Res. 15:2515–2535 (1987)). Cathepsin B has been cloned from human and mouse (Ferrara et al., FEBS Lett. 273:195–199 (1990); Chan et al., Proc. Natl. Acad. Sci. USA 83:7721–7725 (1986)).

A cysteine protease from rabbit osteoclasts was recently cloned, and is structurally related to cathepsins L and S. Tezuka et al., J. Biol. Chem. 269(2):1106 (1994).

Cathepsins are naturally found in a wide variety of tissues. For example, cathepsin L is found in tissues including heart, brain, placenta, lung, skeletal muscle, kidney, liver, testis and pancreas. Cathepsin S is found in lung, liver, spleen and skeletal muscle.

Cathepsins have been implicated in a number of disease conditions. For example, enzymes similar to cathepsins B and L are released from tumors and may be involved in tumor metastasis. Cathepsin L is present in diseased human synovial fluid and transformed tissues. Similarly, the release of cathepsin B and other lysosomal proteases from polymorphonuclear granulocytes and macrophages is observed in trauma and inflammation. Cathepsins have been implicated in arthritis. In addition, cathepsins are found in abnormally high amounts in several tumor cell lines.

Cysteine proteases have also been implicated in bone remodeling. Bone remodeling is a process coupling bone formation and bone resorption, and is part of bone growth. Bone resorption includes demineralization and degradation of extracellular matrix proteins (Delaisse et al., Biochem. J. 279:167–174 (1991)). Type I collagen constitutes ninety-five percent of the organic matrix (Krane et al., in Scientific American Medicine (Rubensttein, E., and Federman, D. D., eds) Vol. 3, 15 Rheumatism, XI Bone Formation and Resorption, pp. 1–26, Scientific American, Inc. New York. In addition to the interstitial collagenase, the lysosomal cysteine proteases cathepsins B and L are thought to be involved in osteoclastic bone resorption (Delaisse et al., 1991, supra). Both enzymes are present in the lysosomes as well as in the acidified extracellular resorption lacuna of the osteoclast (Goto et al., Histochemistry 99, 411–414(1993)) and both proteases display the in vitro ability to degrade collagen Type I at acidic pH (Maciewicz et al., Collagen Rel. Res. 7, 295–304 (1987), Delaisse et aL, (1991), supra). Cysteine protease inhibitors, such as E-64 and leupeptin, have been shown to prevent osteoclastic bone resorption (Delaisse et al., Bone 8, 305–313 (1987), Everts et al., Calcif. Tissue Int. 43, 172–178 (1988)). Cathepsin L is considered to be one of the main proteases involved in collagen degradation in bone (Maciewiecz et al., Biochem. J. 256, 433–440 (1988); Kakegawa et al., FEBS Lett. 321, 247–250 (1993)).

The solid state of bone material is due to the low solubility of hydroxyapatite and other calcium-phosphate bone salts at physiological pH, but bone may break down at acidic pH.

Osteoclasts are multinucleate cells that play key roles in bone resorption. Attached to the bone surface, osteoclasts produce an acidic microenvironment in a tightly defined junction between the specialized osteoclast border membrane and the bone matrix, thus allowing the localized solubilization of bone matrix. This in turn facilitates the protolysis of demineralized bone collagen.

It is thought that the collagenolytic action of cysteine proteases is exerted preferentially in the most acidic part of the bone resorption lacuna close to the ruffled border at a pH around 3.5 or 4.5, whereas the Zn-containing collagenases are more active in the neutral environment at the interface between the demineralized and mineralized matrix (Delaisse et al., supra, (1991)). Besides cathepsins L and B, a variety of cathepsin L- and B-like activities may participate in collagenolytic bone degradation. Page et al. Biochim. Biophys. Acta 1116, 57–66 (1992) isolated multiple forms of cathepsin B from osteoclastomas. These have an acidic pH optimum and the ability to degrade soluble and insoluble Type I collagen. Delaisse et al., 1991, supra, identified a 70 kDa thiol-dependent protease in bone tissue which is also capable of degrading Type I collagen.

Cysteine protease inhibitors have been shown to inhibit osteoclastic bone resorption by inhibiting degradation of collagen fibers. Cathepsins B, L, N and S can degrade type-I collagen at acidic pH. Three cathepsin-type proteases have been isolated from mouse calvaria; putative cathepsins B and L, and a cathepsin L-like:protease (Delaisse et al., Biochem. J. 279:167 (1991). However, it is still unclear as to what cysteine proteases are actually produced by osteoclasts. Recently, a cDNA encoding a novel human cysteine protease was cloned independently by several groups (Shi et al., FEBS Lett. 357, 129–134 (1995), Inaoka et al., Biochem. Biophys. Res. Commun. 206, 89–96 (1995); Brömme and Okamoto, Biol. Chem. Hoppe-Seyler 376, 379–384 (1995)) and named cathepsin O, cathepsin K, and cathepsin O2, respectively.

SUMMARY OF THE INVENTION

It is an object of the present invention to provide for a new class of recombinant cathepsins, cathepsin O2, and variants thereof, and to produce useful quantities of these cathepsin O2 proteins using recombinant DNA techniques.

It is a further object of the invention to provide recombinant nucleic acids encoding cathepsin O2 proteins, and expression vectors and host cells containing the nucleic acid encoding the cathepsin O2 protein.

An addition object of the invention is to provide poly- and monoclonal antibodies for the detection of the presence of cathepsin O2 and diagnosis of conditions associated to cathepsin O2.

A further object of the invention is to provide methods for producing the cathepsin O2 proteins.

In accordance with the foregoing objects, the present invention provides recombinant cathepsin O2 proteins, and isolated or recombinant nucleic acids which encode the cathepsin O2 proteins of the present invention. Also provided are expression vectors which comprise DNA encoding a cathepsin O2 protein operably linked to transcriptional and translational regulatory DNA, and host cells which contain the expression vectors.

Additional aspect of the present invention provides methods for producing cathepsin O2 proteins which comprise culturing a host cell transformed with an expression vector and causing expression of the nucleic acid encoding the cathepsin O2 protein to produce a recombinant cathepsin O2 protein.

A further aspect of the present invention provides poly- and monoclonal antibodies to cathepsin O2 proteins.

BRIEF DESCRIPTION OF THE DRAWINGS

FIGS. 1A, 1B and 1C depict the nucleotide sequence and deduced amino acid sequence of human cathepsin O2 cDNA. The amino acid sequence is shown in single letter code beneath the nucleotide sequence. The active site residues (C25, H159 and N175; papain numbering) are indicated by boldface typing, and the potential N-glycosylation site is underlined once. Arrowheads show the putative post-translational cleavage sites between the presignal and the proregion as well as between the proregion and the mature enzyme. The cleavage between the proregion and the mature protein was confirmed by protein sequencing (double underline).

FIGS. 2A and 2B depict the multiple amino acid sequence alignment of human cathepsin O2 (SEQ ID NO:2) with the human cathepsins S (SEQ ID NO:4) and rabbit OC2(SEQ ID NO:5) (SEQ ID NO:3). * active site residues; boldface type, residue conserved in all known cysteine proteases of the papain family. Amino acids identical in all six proteases are assigned as upper case letters in the consensus sequence, and amino acids identical in five out of six are assigned in lower case letters. Gaps are indicated by hyphens. Numbers indicate the position of the last amino acid in each line and arrowheads show the putative post-translational cleavage sites.

FIG. 3 depicts the maturation of procathepsin O2 with pepsin. Aliquots of the culture supernatant containing procathepsin O2 were incubated with pepsin (0.4 mg/mL) at 40° C. in 100 mM-sodium acetate buffer, pH 4.0. The incubation was stopped by adding sample buffer. The times of digestion are as indicated. Molecular mass standards (kDa) are indicated in the left margin.

FIG. 4 depicts the SDS-PAGE of purified recombinant human cathepsin O2 (Coomassie Blue staining). Lane 1, crude Sf9 fraction; Lane 2, after passage through n-Butyl fast Flow; 3, after passage through Mono S. Molecular mass standards are indicated in the right lane.

FIG. 5 depicts the pH activity profile for recombinant human cathepsin O2. The $k_{cat}/K_m$ values were obtained by measuring the initial rates of Z-FR-MCA hydrolysis and by dividing by enzyme and substrate concentration.

FIG. 6 depicts $k_{cat}/K_m$ values for the hydrolysis of Z-X-R-MCA by cathepsins O2, S, L and B (normalized to the best substrate=1). Cathepsin O2 (Z-LR-MCA) 257,900 $M^{-1}s^{-1}$; cathepsin S (Z-LR-MCA) 243,000 $M^{-1}s^{-1}$; cathepsin L (Z-FR-MCA) 5,111,000 $M^{-1}s^{-1}$); cathepsin B (Z-FR-MCA) 460,000 $M^{-1}s^{-1}$ (data for cathepsins S, L and B from Brömme et al., 1994).

FIG. 7 depicts elastinolytic activity of recombinant human cathepsin O2 and pH 4.5, 5.5 and 7.0 in comparison to cathepsins S and L and pancreatic elastase. The substrate is $^3H$ labelled insoluble elastin.

FIG. 8 depicts northern blot analyses of the hunan cathepsins O2, L and S in osteoclastoma preparations. Lane 1, patient (fibrous and cellular tissue); lane 2, patient 2 (cellular tissue); lane 3, patient 2 (fibrous tissue). Nitrocellulose blots were hybridized with 32P-labelled probes of human cathepsins O2, L and S.

FIGS. 9A and 9B depict SDS PAGE of type I collagen (soluble calf skin collagen) after digestion with recombinant human cathepsin O2 and L and bovine trypsin. FIG. 9A: Collagenase activity: Digestion of soluble calf skin collagen at 28° C. and at pH 4.0, 5.0, 5.5, 6.0, 6.5, 7.0 by human cathepsins O2, S and L (each 50 nM) for 12 hours. The reaction was stopped by addition of 10 µM E-64. Untreated soluble collagen was used as standard (S). FIG. 9B: Gelatinase activity: Digestion of denatured soluble calf skin collagen (10 min heated at 70° C.) at 28° C. and at pH 4.0, 5.0, 5.5, 6.0, 6.5, 7.0 by human cathepsin O2 (0.1 nM), cathepsin L (0.2 nM) and human cathepsin S (1 nM). Molecular mass standards are indicated in the left lane.

FIG. 10 depicts an SDS-PAGE of the purification of the propart of human cathepsin O2.

FIGS. 11A, 11B, 11C, 11D, 11E, 11F, 11G, 11H, 11I, 11J, 11K and 11L depict immunohistochemical staining of human cathepsin O2 in human tissues. (A) osteoclastoma, (B) lung macrophages, (C) bronchiole, (D) endometrium, (E) stomach, (F) colon, (G) kidney, (H) placenta, (I) liver, (J) ovary, (K) adrenal, (L) testis.

DETAILED DESCRIPTION OF THE INVENTION

The present invention provides novel cathepsin O2 proteins and nucleic acids. The cathepsin O2 proteins of the present invention may be identified in several ways. Cathepsin O2 nucleic acids or cathepsin O2 proteins are initially identified by substantial nucleic acid and/or amino acid sequence homology to the sequences shown in FIG. 1. Such homology can be based upon the overall nucleic acid or amino acid sequence.

The cathepsin O2 proteins of the present invention have limited homology to other cathepsins. For example, the mature human cathepsin O2 has roughly 59% homology to mature human cathepsin L, a 58% homology to mature human cathepsin S, a 26% homology to mature human cathepsin B, and a 47% homology to mature human cathepsin H. In addition, the propart of human cathepsin O2 has a 38% homology to the propart of human cathepsin L, a 51% homology to the propart of human cathepsin S, a 13% homology to the propart of human cathepsin B, and a 23% homology to the propart of human cathepsin H. In addition, the human cathepsin O2 protein has roughly 90% homology to a rabbit osteoclast protein.

As used herein, a protein is a "cathepsin O2 protein" if the overall homology of the protein sequence to the amino acid sequence shown in FIG. 1 is preferably greater than about 90%, more preferably greater than about 95% and most preferably greater than 98%. This homology will be determined using standard techniques known in the art, such as the Best Fit sequence program described by Devereux et al., Nucl. Acid Res. 12:387–395 (1984). The alignment may include the introduction of gaps in the sequences to be aligned. In addition, for sequences which contain either more or fewer amino acids than the protein shown in FIG. 1, it is understood that the percentage of homology will be determined based on the number of homologous amino acids in relation to the total number of amino acids. Thus, for example, homology of sequences shorter than that shown in FIG. 1, as discussed below, will be determined using the number of amino acids in the shorter sequence.

In a preferred embodiment, the cathepsin O2 proteins of the present invention are human cathepsin O2 proteins.

Cathepsin O2 proteins of the present invention may be shorter than the amino acid sequence shown in FIG. 1. As shown in Example 2, the human cathepsin O2 protein may undergo post-translational processing similar to that seen for cathepsins B and S, and papain (Brömme et al., J. Biol. Chem. 268:4832–4838 (1993); Vernat et al., J. Biol. Chem. 266:21451–21457 (1991); and Rowan et al., J. Biol. Chem. 267:15993–15999 (1992)). The cathepsin O2 protein is made as a preproprotein, with a traditional presequence, a prosequence or "propart", and the mature sequence. These are depicted in FIG. 1, with the sequence of human cathepsin O2, including the pre, pro and mature coding sequences, shown in FIG. 1. The presequence comprises the first 15 amino acids of the sequence shown in FIG. 1, the propart spans from amino acid 16 to amino acid 114 (98 amino acids), and the mature protein spans from position 115 to 329 (215 amino acids). The prosequence, or propart, is hypothesized to serve as an inhibitor of the enzyme until the enzyme is activated, most probably as a result of a change in pH. The proteolytic processing of the propart is autoproteolytic for papain (Vernet et al., supra), cathepsin S and cathepsin L. The definition of cathepsin O2 includes preprocathepsin O2, procathepsin O2, mature cathepsin O2, and the propart, separate from the mature cathepsin O2.

In a preferred embodiment, also included within the definition of cathepsin O2 proteins are portions or fragments of the sequence shown in FIG. 1. In one embodiment, the fragments range from about 40 to about 200 amino acids. Preferably, the fragments are not identical to the rabbit osteoclast protein of Tezuka et al., supra, and at least about 95–98% homologous to the human cathepsin O2 protein. In a preferred embodiment, when the cathepsin O2 protein is to be used to generate antibodies, for example for diagnostic purposes, the cathepsin O2 protein must share at least one epitope or determinant with either the propart or the mature protein shown in FIG. 1. By "epitope" or "determinant" herein is meant a portion of a protein which will generate and bind an antibody. Thus, in most instances, antibodies made to a smaller cathepsin O2 protein will be able to bind to the full length protein. In a preferred embodiment, the antibodies are generated to a unique epitope; that is, the antibodies exhibit little or no cross reactivity to other proteins such as other cathepsin proteins, or to cathepsins from other organisms.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 1 is preferably greater than 65%, more preferably greater than about 75% and most preferably greater than 85%. In some embodiments the homology will be as high as about 95 to 98 or 99%.

In one embodiment, the nucleic acid homology is determined through hybridization studies. Thus, for example, nucleic acids which hybridize under high stringency to the nucleic acid sequences shown in FIG. 1 are considered cathepsin O2 genes. High stringency conditions are generally 0.1×SSC at 37–65° C.

In another embodiment, less stringent hybridization conditions are used; for example, reduced stringency conditions are generally 2×SSC and 0.1%SDS.

The cathepsin O2 proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the corresponding non-coding strand of the nucleic acid sequence shown in FIG. 1, but may contain ribonucleotides as well as deoxyribonucleotides. Generally, anti-sense nucleic acids function to prevent expression of mRNA, such that a cathepsin O2 protein is not made. The nucleic acid may be double stranded, single stranded, or contain portions of both double stranded or single stranded sequence.

By the term "recombinant nucleic acid" herein is meant nucleic acid, originally formed in vitro by the manipulation of nucleic acid by endonucleases, in a form not normally found in nature. Thus an isolated cathepsin O2 protein gene, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. Thus, for example, cathepsin O2 proteins which are substantially or partially purified, or are present in the absence of cells, are considered recombinant. The definition includes the production of a cathepsin O2 protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions.

Also included with the definition of cathepsin O2 protein are cathepsin O2 proteins from other organisms, which are cloned and expressed as outlined below.

In the case of anti-sense nucleic acids, an anti-sense nucleic acid is defined as one which will hybridize to all or part of the corresponding non-coding sequence shown in FIG. 1. Generally, the hybridization conditions used for the determination of anti-sense hybridization will be high stringency conditions, such as 0.1×SSC at 65° C.

Once the cathepsin O2 protein nucleic acid is identified, it can be cloned and, if necessary, its constituent parts recombined to form the entire cathepsin O2 protein nucleic acid. Once isolated from its natural source, e.g., contained within a plasmid or other vector or excised therefrom as a linear nucleic acid segment, the recombinant cathepsin O2 protein nucleic acid can be further used as a probe to identify and isolate other cathepsin O2 protein nucleic acids. It can also be used as a "precursor" nucleic acid to make modified or variant cathepsin O2 protein nucleic acids and proteins.

Using the nucleic acids of the present invention which encode cathepsin O2 protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the cathepsin O2 protein. "Operably linked" in this context means that the transcriptional and translational regulatory DNA is positioned relative to the coding sequence of the cathepsin O2 protein in such a manner that transcription is initiated. Generally, this will mean that the promoter and transcriptional initiation or start sequences are positioned 5' to the cathepsin O2 protein coding region. The transcriptional and translational regulatory nucleic acid will generally be appropriate to the host cell used to express the cathepsin O2 protein; for example, transcriptional and translational regulatory nucleic acid sequences from Bacillus will be used to express the cathepsin O2 protein in Bacillus. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The cathepsin O2 proteins of the present invention are produced by culturing a host cell transformed with an expression vector containing nucleic acid encoding a cathepsin O2 protein, under the appropriate conditions to induce or cause expression of the cathepsin O2 protein. The conditions appropriate for cathepsin O2 protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, HeLa cells, and immortalized mammalian myeloid and lymphoid cell lines.

In a preferred embodiment, cathepsin O2 proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of cathepsin O2 protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the cathepsin O2 protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, cathepsin O2 proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the cathepsin O2 protein; a wild type baculovirus with a sequence homologous to the baculovirus-specific fragment in the transfer vector (this allows for the homologous recombination of the heterologous gene into the baculovirus genome); and appropriate insect host cells and growth media.

Mammalian expression systems are also known in the art and are used in one embodiment. A mammalian promoter is any DNA sequence capable of binding mammalian RNA polymerase and initiating the downstream (3') transcription of a coding sequence for cathepsin O2 protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, cathepsin O2 protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant cathepsin O2 protein may be expressed intracellularly or secreted. The cathepsin O2 protein may also be made as a fusion protein, using techniques well known in the art. Thus, for example, if the desired epitope is small, the cathepsin O2 protein may be fused to a carrier protein to form an immunogen. Alternatively, the cathepsin O2 protein may be made as a fusion protein to increase expression, or for other reasons.

Also included within the definition of cathepsin O2 proteins of the present invention are amino acid sequence variants. These variants fall into one or more of three classes: substitutional, insertional or deletional variants. These variants ordinarily are prepared by site specific mutagenesis of nucleotides in the DNA encoding the cathepsin O2 protein, using cassette mutagenesis or other techniques well known in the art, to produce DNA encoding the variant, and thereafter expressing the DNA in recombinant cell culture as outlined above. However, variant cathepsin O2 protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the cathepsin O2 protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cathepsin O2 protein variants screened for the optimal combination of desired activity. Techniques for making substitution mutations at predetermined sites in DNA having a known sequence are well known, for example, M13 primer mutagenesis. Screening of the mutants is done using assays of cathepsin O2 protein activities; for example, purified or partially purified cathepsin O2 may be used in kinetic assays such as those depicted in the examples, to determine the effect of the amino acid substitutions, insertions or deletions. Alternatively, mutated cathepsin O2 genes are placed in cathepsin O2 deletion strains and tested for cathepsin O2 activity, as disclosed herein. The creation of deletion strains, given a gene sequence, is known in the art.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as for example when the prosequence or the mature part of the cathepsin O2 protein is deleted. In addition, as outlined above, it is possible to use much smaller fragments of the cathepsin O2 protein to generate antibodies.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the cathepsin O2 protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. icucyl, isolcucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the polypeptide as needed. Alternatively, the variant may be designed such that the biological activity of the cathepsin O2 protein is altered. For example, the proteolytic activity of the cathepsin O2 protein may be altered, through the substitution of the amino acids of the catalytic triad. The catalytic triad, consisting of a cysteine at position 25, a histidine at position 162 and an asparagine at position 182, may be individually or simultaneously altered to decrease or eliminate proteolytic activity.

This may be done to decrease the toxicity of administered cathepsin O2. Similarly, the cleavage site between the prosequence and the mature sequence may be altered, for example to eliminate proteolytic processing.

In a preferred embodiment, the cathepsin O2 protein is purified or isolated after expression. Cathepsin O2 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the cathepsin O2 protein may be purified using a standard anti-cathepsin O2 antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the cathepsin O2 protein. In some instances no purification will be necessary.

In some embodiments, the cathepsin O2 enzyme is expressed as a proenzyme. As depicted in the examples, the proenzyme may be treated with exogenous protease to convert the enzyme to the mature, active form, as is known in the art. Suitable exogenous proteases include, but are not limited to, pepsin and cathepsin D.

Once expressed and purified if necessary, the cathepsin O2 proteins are useful in a number of applications.

For example, as shown in Example 5, the cathepsin O2 proteins of the present invention have collagenase activity. Thus, the cathepsin O2 proteins may be used as a collagenase, both in vitro and in vivo. For example, cathepsin O2 may be used to treat analytical samples which contain interfering or problematic levels of collagen.

Similarly, cathepsin O2 proteins may be used to degrade excess collagen within the body. There are a variety of conditions associated with excess collagen. For example, one treatment of spinal disk problems such as severe disk inflammation and herniation involves the injection of collagenase or chymopapain to degrade the disk collagen (Leonardo et al., Ann. Chirm Gyneacol. 82:141–148 (1993); Gogan et al., Spine 17:388–94 (1992); Stula, Nerochirurgia 33:169–172 (1990); and Boccanera et al., Chir. Organi. Mov. 75:25–32 (1990)). Alternatively, the treatment of adhesions, such as pelvic adhesions, post surgical adhesions, pulmonary adhesions, abdominal adhesions and the like may be treated or dissolved with cathepsin O2. Similarly, scars and keloids may be treated with cathepsin O2 to remove or decrease the excessive amounts of collagen present. In addition, endometriosis is another significant clinical problem involving the deposit of excess amounts of collagen and other substances within the uterus and surrounding tissue; certain forms of endometriosis may also be treated with the cathepsin O2 of the present invention.

In an alternative embodiment, cathepsin O2 may be used to dissolve the matrices around tumors. Generally, tumor pH is lower than physiological pH, and, as outlined in the Examples, cathepsin O2 is active at acidic pH. Therefore, cathepsin O2 is suited to dissolve the collagen-based matrix generally surrounding a tumor.

In one embodiment, the cathepsin O2 proteins of the present invention may also be administered to treat pycnodysostosis, an osteopetrosislike bone disorder. This disorder appears to be caused by insufficient activity of osteoclastic cysteine-proteinases. In some embodiments, gene therapy may be used to administer the cathepsin O2.

In addition, since cathepsin O2 is functional at acidic pH, cathepsin O2 can be administered in conjunction with bone demineralization compounds, such as acids, to degrade bone tissue. Thus, aberrant or excess bone growths may be treated.

The cathepsin O2 proteins of the present invention are also useful to screen for cathepsin O2 protease inhibitors and for cysteine protease inhibitors. Cysteine protease inhibitors have a variety of uses, as will be appreciated in the art, including purification of cysteine proteases via coupling to affinity chromatography columns, and inhibition of cysteine proteases, similar to known cysteine protease inhibitors. In addition, cysteine protease inhibitors may have therapeutic uses, since a wide variety of physiological disorders are associated with increased levels of cysteine proteases, including arthritis, inflammation, osteoporosis, muscular dystrophy, tumor invasion, multiple myeloma and glomerulonephritis, as is known in the art.

In a preferred embodiment, the propart of cathepsin O2 may be used as a specific inhibitor of cathepsin O2. Thus, for example, the propart may be separately expressed, that is, without the mature sequence, and used as a highly specific tight-binding inhibitor of cathepsin O2, as is shown in Example 3. Thus, the propart may be added therapeutically to samples or tissues which contain excess cathepsin O2; for example, in the treatment of bone disorders or tumors, as outlined below.

In one embodiment, the propart of cathepsin O2 is labeled, and used to diagnose, quantify or identify the presence of cathepsin O2 within a sample or tissue.

Additionally, the cathepsin O2 proteins may be used to generate polyclonal and monoclonal antibodies to cathepsin O2 proteins, which are useful as described below. Similarly, the cathepsin O2 proteins can be coupled, using standard technology, to affinity chromatography columns. These columns may then be used to purify cathepsin O2 antibodies.

In a preferred embodiment, monoclonal antibodies are generated to the cathepsin O2 protein, using techniques well known in the art. As outlined above, the antibodies may be generated to the full length cathepsin O2 protein, or a portion of the cathepsin O2 protein.

In a preferred embodiment, the antibodies are generated to epitopes unique to the human cathepsin O2 protein; that is, the antibodies show little or no cross-reactivity to antibodies generated to cathepsin O2 proteins from other organisms, such as cathepsins from rabbits or rats.

These antibodies find use in a number of applications. In a preferred embodiment, the antibodies are used to diagnose the presence of cathepsin O2 in a sample or patient. For example, an excess of cathepsin O2 protein, such as may exist in osteoclast related disorders and bone diseases, as well as tumors, may be diagnosed using these antibodies.

Similarly, high levels of cathepsin O2 are associated with certain ovarian or cervical carcinomas, as evidenced by high levels of cathepsin O2 in HeLa cells. Thus, these types of tumors may be detected or diagnosed using the antibodies of the present invention.

The detection of cathepsin O2 will be done using techniques well known in the art; for example, samples such as blood or tissue samples may be obtained from a patient and tested for reactivity with labelled cathepsin O2 antibodies, for example using standard techniques such as RIA and ELISA.

In one embodiment, the antibodies may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the cathepsin O2 protein antibody may be labelled for detection, or a secondary antibody to the cathepsin O2 protein antibody may be created and labelled.

In one embodiment, the antibodies generated to the cathepsin O2 proteins of the present invention are used to purify or separate cathepsin O2 proteins from a sample. Thus for example, antibodies generated to cathepsin O2 proteins may be coupled, using standard technology, to affinity chromatography columns. These columns can be used to pull out the cathepsin O2 protein from tissue samples.

Recent work has suggested that cysteine proteases may be used as DNA binding transcription factors (Xu et al., supra). In some embodiments, the cathepsin O2 proteins of the present invention may be used as transcription factors.

The parasite *Paragonimus westermani* was recently shown to express an immunosuppressor with homology to cysteine proteases (Hamajima et al., supra). In fact, the homology to the cathepsin O2 proteins of the present invention is roughly 40%. Thus, in one embodiment, the cathepsin O2 proteins may be useful as immunosuppressors.

In a preferred embodiment, when the cathepsin O2 proteins are to be administered to a human, the cathepsin O2 proteins are human cathepsin O2 proteins. This is therapeutically desirable in order to ensure that undesirable immune reactions to the administered cathepsin O2 are minimized.

The administration of the cathepsin O2 protein of the present invention can be done in a variety of ways, including, but not limited to, orally, subcutaneously, intravenously, intranasally, transdermally, intraperitoneally, intramuscularly, intrapulmonary, vaginally, rectally, or intraocularly.

The pharmaceutical compositions of the present invention comprise a cathepsin O2 protein in a form suitable for administration to a patient. The pharmaceutical compositions may include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The pharmaceutical compositions of the present invention are generally administered at therapeutically effective dosages, as can be routinely determined by those in the art.

It is believed that the human cathepsin O2 protein of the invention has characteristics which render the human protein more acceptable than cathepsin O2 proteins from other species for therapeutic purposes. In particular, the antigenicity of cathepsin O2 proteins from other species in humans makes these proteins less acceptable as therapeutic compositions; i.e. cathepsins from other species may elicit undesirable immunological responses in humans.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are incorporated by reference.

EXAMPLES

Example 1

Cloning of Human Cathepsin O2

Unless otherwise specified, all general recombinant DNA techniques followed the methods described in Sambrook et al. (Molecular Cloning, A Laboratory Manual, Cold Spring Harbor Press, 1989).

Two degenerate PCR primers were designed based on the published sequence of a rabbit osteoclastin gene (Tezuko et al. 1994):

5'-GGA-TAC-GTT-ACN-CCN-GT-3' (SEQ ID NO:8)
5'-GC-CAT-GAG-G/ATA-NCC-3' (SEQ ID NO:9)

These primers were used for screening a human spleen Quick Clone cDNA preparation (Clontech). An amplified 450 base pair fragment was isolated and purified and used as a cDNA probe for screening a human spleen cDNA library (gt10 from Clontech). 600,000 clones were screened on 20 filters using a technique in which the plaques reform directly on the filter (Woo, Methods Enzymol. 68:389–395 (1979)). This allows an amplification of the signal from positive plaques allowing for shorter exposure times, thus decreasing background and the visualization of false positives. The filters were washed at moderate stringency conditions: once with 2×SSC, 0.1%SDS at room temperature for 10 min and once with 2×SSC, 0.1% SDS at 68° C. for 20 min.

Phages from two positive plaques were isolated and cloned into the EcoRI site of pBluescript SK+ vector (Stratagene).

One positive clone was completely sequenced on an ABI sequencer model 373A; the sequence is shown in FIG. 1. Sequence alignments of the protein of human cathepsin O2 (SEQ ID NO:2), human cathepsin S (SEQ ID NO:4) and human cathepsin L (SEQ ID NO:5) are shown in FIG. 2.

Example 2

Expression of Human Cathepsin O2

The human cathepsin O2 cDNA was cloned into the polyhedrin gene of the baculovirus transfer vectors using standard methods. The cDNA encoding the complete open reading frame of the prepro enzyme was inserted into the BglII and BamHI site of the pVL1392 transfer vector (PharMingen). Recombinant baculoviruses were generated by homologous recombination following co-transfection of the baculovirus transfer vector and linearized AcNPV genomic DNA (PharMingen) into Sf9 cells. Following end point dilution human cathepsin O2 expression is measured in a fluorimetric substrate assay, outlined below.

Pure virus (AcNPVCO2) was obtained by plaque purification. Sf9 cells were grown in Sf900II media (Gibco BRL, Grand Island, N.Y.) to a density of $2 \times 10^6$ cells/ml and infected at a moi of 1. Total cell number and cellular as well as secreted activity of cathepsin O2 were monitored every 24 h. After 3.5 days the cells were harvested.

The majority of immunoreactive material of about 43 kDa was found within the infected cells. In contrast to the single product of 43 kDa in the culture medium an additional slight band of 44 kDa was detected in the cellular extract. The higher molecular weight band putatively represents unprocessed preprocathepsin O2 whereas the 43 kDa protein putatively is proenzyme. No activity was observed immediately after lysis of the cells nor during autoactivating conditions at 40° C. between pH 4.0 and 4.5 in the presence of dithiothreitol using the synthetic substrate Z-FR-MCA at pH 7.5. The increase of an E-64 inhibitable activity under autoactivating conditions and measured at pH 5.5 was assigned to an endogenous Sf9 cysteine protease (unpublished results). No processing of the cathepsin O2 precursor was observed with human cathepsin B incubated at pH's 4.0 and 5.5 for 2 hours at 37° C. (data not shown).

Activation Purification and N-terminal Sequencing of Recombinant Human Cathepsin O2

The intracellular cathepsin O2 was produced within the SF9 cells as an inactive precursor. The enzyme was activated in the cell lysate under reducing and acidic conditions as follows. The Sf9 cells were harvested from the production media by centrifugation at 2,000×g and were lysed in a Dounce homogenizer. The cell lysate containing the inactive cathepsin O2 precursor was brought up to 100 ml with 100 mM-sodium acetate buffer, pH 3.75 containing 0.5% triton X-100, 5 mM-dithiothreitol and 2.5 mM-$Na_2$EDTA and the pH was adjusted to 4.0. The conversion of the proform into the active enzyme was accomplished by treatment with pepsin. After addition of porcine pepsin (Sigma, St. Louis, Mo.) at a final concentration of 0.4 mg/mL the activation mixture was incubated in a shaker for 90 min at 40° C. at 200 rpm. The activation was monitored using Z-FR-MCA (10 $\mu$M) as a fluorogenic substrate measured in 100 mM Tris/HCl buffer, pH 7.5.

The precursor of cathepsin O2 was efficiently transformed into mature active enzyme by treatment with pepsin at pH 4.0. The digest of crude cellular extract or of concentrated culture media supernatant resulted in a time-dependent disappearance of precursor and generation of mature enzyme (29 kD) via an intermediate of 36 kD (FIG. 3). In parallel with this process an increase of E-64 inhibitable activity measured at pH 7.5 was observed.

No activation of the precursor was observed by addition of purified active cathepsin O2 at pH 4.5 (data not shown) indicating that neither a cis nor trans autoactivation of cathepsin O2 within the lysosomes is likely. This contrasts related cysteine proteases such as papain and cathepsin S which exhibit a potential autocatalytic activation pathway (Vernet et al., J. Biol. Chem., 265:1661–1666 (1990), Brömme et al., J. Biol. Chem. 268:4832–4838 (1993)). A natural activating enzyme of cathepsin O2 within the osteoclast could be the aspartyl protease cathepsin D which is present in osteoclastic lysosomes but secreted at low levels into the resorption lacuna (Goto et al., 1993).

The activated lysate was adjusted to pH 7.0 with 2M Tris base, clarified by centrifugation at 10,000×g and the supernatant was adjusted to 2.5 M ammonium sulfate at pH 5.5. After centrifugation at 16,000×g the cleared supernatant was concentrated to 50 mL by ultrafiltration (YM10 Amicon). After additional centrifugation at 10,000×g, the cleared supernatant was loaded onto butyl Sepharose 4 Fast Flow (Pharmacia, Sweden) and the column was washed with an ammonium sulfate gradient (2.5 M to 0 M in 25 mM acetate buffer, pH 5.5). The activity was eluted at 0 M ammonium sulfate. The pooled and concentrated fractions were than applied to an FPLC Mono S column (Pharmacia, Sweden) and eluted with a linear NaCl gradient (0–2 M) in 20 mM sodium acetate, pH 5.5. Electrophoretically homogeneous cathepsin O2 was eluted at 1.4M NaCl The average yield of a IL Sf9 cell culture (appr. $2 \times 10^9$ cells) was approximately 1 mg purified enzyme (Table 1).

TABLE I

Purification of recombinant human cathepsin O2[a]

| Assay | Total protein mg | Total activity μMol/min | Specific activity μMol/ mg/min | Purification factor | Yield % |
|---|---|---|---|---|---|
| Crude[b] | 800 | 1,753 | 2.2 | 1 | 100 |
| 2.5 M (NH$_4$)$_2$SO$_4$ soluble fraction | 276 | 1,412 | 5.1 | 2.3 | 81 |
| Butyl Sepharose 4 | 2.9 | 1,143 | 394 | 179 | 65 |
| MonoS | 1.1 | 512 | 465 | 211 | 29 |

[a] from 1 L Sf9 culture
[b] after activation with pepsin

The purified enzyme was a single chain enzyme and exhibited an apparent molecular weight of 29 kDa in a 4–20% Tris/Glycine SDS gel under reducing conditions. Treatment with endoglycosidases H and F as well as N-glycosidase F did not result in a shift in the molecular weight which implies that the protease is not glycosylated (data not shown). Human cathepsin O2 has two potential glycosylation sites in its mature sequence. However, both sites have either a proline residue consecutive to the asparagine or to the threonine, so that their use is unlikely. Cathepsin O2 contains furthermore one putative glycosylation site in the propart close to the processing site between the mature enzyme and the propart. Again, no shift in molecular weight of the proenzyme was observed after overnight treatment with endoglycosidases H and F as well as N-glycosidase F.

NH$_2$-terminal sequencing was carried out by automated Edman degradation. N-terminal sequencing of the mature protease revealed the natural processing site for cysteine proteases of the papain family with a proline adjacent to the N-terminal alanine (NH$_2$-APDSVDYRKKGYVTPVKN) (SEQ ID NO:10). In contrast, autocatalytically activated cysteine proteases frequently have at their processing site an N-terminal extension of 3 to 6 amino acids from the propart (Brömme et al. 1993). The calculated molecular mass of mature cathepsin O2 would be 23,495 which seems to be the actual weight of the enzyme. Trypsin (24 kDa) displayed the same apparent molecular weight of 29 kDa when tested under analogous conditions.

Recombinant human cathepsin S was expressed using the baculovirus expression system and purified as described elsewhere (Brömme and McGrath, unpublished results). Recombinant human cathepsin L was kindly provided by Dr. Mort, Shriner's Hospital for Crippled Children, Montreal, Quebec). All cathepsins used were electrophoretically homogeneous and their molarities were determined by active-site titration with E-64 as described by Barrett and Kirschke (1981).

Fluorimetric Enzyme Assay

Human cathepsin O2 was assayed with a fluorogenic substrate Z-FR-MCA(MCA, methyl coumarylamide) in 100 mM sodium acetate buffer, containing 2.5 mM dithioerythreitol and 2.5 mM EDTA. Initial rates of hydrolysis of the MCA-substrate are monitored in 1-cm cuvettes at 25° C. at an excitation wavelength at 380 nm and an emission wavelength at 450 nm. The concentration of Z-FR-MCA is 5 μM under standard conditions.

The kinetic constants $V_{max}$ and $K_m$ were obtained by non-linear regression analysis using the program Enzfitter (Leatherbarrow, Enzfitter, Elsevier Biosoft, Cambridge, United Kingdom (1987).

The inhibition of cathepsin O2 was assayed at a constant substrate (5 μM Z-FR-MCA) and enzyme concentration (1 nM) in the presence of different inhibitor concentrations in the substrate assay buffer. Cathepsin O2 was preincubated with the inhibitors for 10 min and the reaction was started with substrate. The residual activity was monitored and percent inhibition was calculated from the uninhibited rate.

Example 3

Cloning and Expression of the Propart of Cathepsin O2

The propart of human cathepsin O2 was amplified by PCR using standard techniques using the following primers:

5'-CTG GAT CCC TGT ACC CTG AGG AGA TAC TG-3' (SEQ ID NO:11)

5'-CTA AGC TTC TAT CTA CCT TCC CAT TCT GGG ATA-3' (SEQ ID NO:12)

The proregion was expressed in the pTrcHis vector (Invitrogen Corp., San Diego, Calif.), which contains a series of six histidine residues that function as a metal binding domain in the translated protein. This metal binding domain was used to purify the propart of cathepsin O2 over Invitrogen's ProBond Resin included in their Xpress system Protein Expression kit. A gel of the purified propart is shown in FIG. 10.

The purified propart inhibited the parent enzyme with a $K_i$ value of 0.1 nM.

Example 4

Antibodies to Human Cathepsin O2 and Immunohistochemistry

Polyclonal antibodies were made in New Zealand white rabbits to the proenzyme of human cathepsin O2. The cDNA encoding the proenzyme was amplified by PCR from a preparation of its preproenzyme sequence using Pfu DNA polymerase (Promega). The primers used were made to the 5' end of the proenzyme with an NheI site and to the 3' end with a BamHI site. Human cathepsin O2 was cloned and expressed in E. coli (BL21(DE3)) in the pET11c vector from Novagen. Expression was induced with 0.4 mM IPTG at OD600=0.6 and cells were harvested 2 hours after induction. After collection, the expressed proteins were run on Novex 12% Tris-Glycine SDS gels which were Coomassie stained and destained. The proenzyme band of cathepsin O2 which was confirmed by N-terminal sequencing was cut out. The protein was electroeluted from the gel slices and concentrated on a Centricon10 which was pretreated with 1×elution buffer. The antigen was brought up to 1 ml in 1×PBS and used for immunization (EL Labs, Soquel, Calif.).

The antibodies were purified from the whole serum with acetone powder made to an induced culture of BL21(DE3) and by affinity binding to and elution from the antigen on nitrocellulose. The purified antibodies were specific for human procathepsin O2, the propart, and for the mature enzyme, and do not exhibit cross-reactivity with human cathepsins S, L and B in Western Blot analysis at a 1:2000 dilution.

Formalin fixed and paraffin-embedded human tissue sections (Biogenex, San Ramon, Calif.) were prepared as described previously (Cattoretti et al., 1992) and were stained with control rabbit IgG or affinity purified anticathepsin O2 antibodies using the StrAviGen detection system (Biogenex). Section were counterstained with Mayer's hematoxylin.

Immunostaining of an osteoclastoma revealed an intense specific staining of multinucleated osteoclasts whereas stromal cells displayed no reaction (FIG. 11). Intense immunohistochemical staining of osteoclasts in prenatal human bones was also observed (data not shown). In lung, cathepsin O2 was detected at two sites; first in lung alveolar macrophages (FIG. 11) and second in bronchiolar epithelial cells. Cathepsin O2 was found also in epithelial cells of gastric glands in stomach, of intestinal glands in colon, of proximal and distal tubuli in kidney and in the epithelium of the uterine glands in the endometrium. Furthermore, Kupfer cells in liver as well as developing sperm cells in testis exhibit a strong staining against cathepsin O2. A more uniform staining was observed in the cortex of the adrenal, in ovary and placenta (FIG. 11).

Similarly, polyclonal antibodies against the electrophoretically homogenous propart of human cathepsin O2 are produced in New Zealand white rabbits, and monoclonal antibodies to the propart, procathepsin O2 and mature cathepsin O2 by standard techniques.

Example 5

Characterization of Human Cathepsin O2

The following experiments were done with the partially purified human cathepsin O2 of example 2.

pH Activity Profile and pH-stability of Recombinant Human Cathepsin O2

The pH-stability of cathepsin O2 was determined by incubation of the active protease at different pH values in presence of 5 mM dithioerythreitol and 5 mM EDTA at 25° C. The residual activity was measured in time intervals using the above described fluorimetric substrate assay.

Initial rates of substrate hydrolysis were monitored as described above. The pH activity profile of human cathepsin O2 was obtained at 1 $\mu$M substrate (Z-FR-MCA) concentration ($[S]<<K_m$ where the initial rate $v_o$ is directly proportional to the $k_{cat}/K_m$ value). The following buffers were used for the pH activity profile: 100 mM sodium citrate (pH 2.8–5.6) and 100 mM sodium phosphate (pH 5.8–8.0). All buffers contained 1 mM EDTA and 0.4 M NaCl to minimize the variation in ionic strength. A three protonation model (Khouri et al., Biochem. 30:8929–8936 (1991)) was used for least square regression analysis of the pH activity data. The data were fitted to the following equation.

$$(k_{cat}/K_m)_{obs}=(k_{cat}/K_m)/([H^+]/K_1+1+K_2/[H^+])$$

The pH stability of cathepsins O2, S and L was studied at three different pH values. Recombinant human cathepsins O2, S and L were incubated at 37° C. in 100 mM sodium acetate buffer, pH 5.5, in 100 mM potassium phosphate buffer, pH 6.5 and in 100 mM Tris/HCl, pH 7.5 containing 5 mM dithiothreitol and 2.5 mM EDTA. Incubating for 0.5, 1, 2 and 4 hours, the activity remaining was determined using 5 $\mu$M Z-FR-MCA for cathepsin O2 (100 mM potassium phosphate buffer, pH 6.5) and cathepsin L (100 mM sodium acetate buffer, pH 5.5) and 5 $\mu$M Z-VVR-MCA for cathepsin S (100 mM potassium phosphate buffer, pH 6.5).

Profiles of pH activity are sensitive measures of enzymatic functional and structural integrity. A comparison of pH profiles from different but related proteases reveals differences in intrinsic activity and stability of these proteases. Human cathepsin O2 displays a bell-shaped pH profile with flanking pK values of 4.0 and 8.13 (Table 2; FIG. 5).

TABLE 2 pK values of pH activity profile of recombinant human cathepsin O2 in comparison with pK values described for cathepsins S and L and papain

| Protease | pK$_1$' | pK$_1$ | pK$_2$ | pH optimum[a] |
|---|---|---|---|---|
| human cathepsin O2 | 3.43 ± 0.05 | 4.00 ± 0.02 | 8.13 ± 0.01 | 6.1 |
| human cathepsin S[b] | | 4.49 ± 0.03 | 7.82 ± 0.03 | 6.1 |
| human cathepsin L[b] | 3.33 ± 0.14 | 4.22 ± 0.28 | 6.95 ± 0.09 | 5.6 |
| papain[c] | 3.58 ± 0.29 | 4.54 ± 0.29 | 8.45 ± 0.02 | 6.5 |

[a]calculated from (pK$_1$ + pK$_2$)/2
[b]from Brömme et al., 1993, supra
[c]from Khouri et al., 1991, supra The pH optimum of Human cathepsin O2 was between 6.0 and 6.5 and comparable to that observed for cathepsin S (Brömme et al., supra, 1993). The width of the pH profile, which mirrors the stability of the ion-pair (Menard et al., Biochem. 30:5531–5538 (1991)), is 4.15 for cathepsin O2 but only 3.35 for cathepsin S (Brömme et al., 1993, supra). This parameter for human cathepsin O2 is more similar to that observed for the very stable papain which displays a profile width of 3.91 (Khouri et al., supra, 1991).

Human cathepsin O2 was more stable than cathepsin L at slightly acidic to neutral pH values but less stable than cathepsin S (Table 3).

TABLE 3 pH stability at 37° C. of recombinant human cathepsin O2 in comparison with recombinant human cathepsins S and L.

| Protease | Incubation time hr | Residual activity (%) | | |
|---|---|---|---|---|
| | | pH 5.5 | pH 6.5 | pH 7.5 |
| cathepsin O2 | 0.5 | 91 | 85 | 11 |
| | 1 | 88 | 49 | 0 |
| | 2 | 70 | 22 | 0 |
| | 4 | 52 | 15 | 0 |
| cathepsin S | 0.5 | 100 | 100 | 91 |
| | 1 | 95 | 100 | 72 |
| | 2 | 92 | 94 | 61 |
| | 4 | 83 | 71 | 60 |
| cathepsin L | 0.5 | 87 | 12 | 0 |
| | 1 | 78 | 3 | 0 |
| | 2 | 71 | 0 | 0 |
| | 4 | 51 | 0 | 0 |

Approximately 50% of the cathepsin O2 activity remained after I hour at 37° C. and pH 6.5 whereas essentially no cathepsin L activity could be observed under these conditions.

However, it must be considered that the pH stability was determined without substrate protection which usually increases the pH stability. In the $^3$H elastin degradation assay with cathepsin O2 an increase of solubilized $^3$H fragments was still observed after 2 hours at pH 7.0.

Inhibitor Profile of Recombinant Human Cathepsin O2

The efficacy of protease class specific inhibitors to inhibit cathepsin O2 was determined by adding the inhibitor to the purified enzyme in a fluorimetric enzyme assay (described above).

Human cathepin O2 displays a typical inhibitor profile of a cysteine protease. It is inhibited by cystein protease inhibitors and by inhibitors of both cysteine and serine proteases (Table 4). At concentrations above 0.1 $\mu$M, peptide aldehydes, diazomethanes E-64 and chicken cystatin completely inhibit enzyme activity. On the other hand, specific serine and aspartic protease inhibitors did not affect enzyme activity. No effect of EDTA at a concentration of 4 mM was observed on the activity of cathepsin O2. At higher concentrations (>5 mM) a partial non-specific inhibition was observed.

TABLE V

Inhibitor profile of recombinant human cathepsin O2

|  | inhibitor | [inhibitor] | % inhibition |
|---|---|---|---|
| serine protease inhibitors | PMSF | 1 mM | 0 |
|  | Befablock | 0.2 mM | 0 |
|  | DCI | 0.1 mM | 0 |
| serine/cysteine protease inhibitors | leupeptin | 0.05 µM | 85 |
|  | chymostatin | 0.05 µM | 64 |
|  | calpeptin | 0.1 µM | 100 |
| aspartate protease inhibitor | pepstatin | 0.1 µM | 0 |
| metallo-protease inhibitor | EDTA | 4 mM | 0 |
| cysteine protease inhibitor | iodo acetate | 50 µM | 60 |
|  | Z-FF-CHN$_2$ | 0.1 µM | 90 |
|  | Z-FA-CHN$_2$ | 0.1 µM | 100 |
|  | E-64 | 0.1 µM | 100 |
|  | chicken cystatin | 0.1 µM | 100 |

Cathepsin O2 activity is only inhibited by cysteine protease specific inhibitors.

Substrate Specificity of Recombinant Human Cathepsin O2

The substrate specificity towards synthetic substrates was determined using the above described substrate assay.

The $S_2P_2$ specificity of human cathepsin O2 was characterized using synthetic substrates of the type Z-X-R-MCA with X equal to F, L, V or R. The $S_2$ subsite pocket of cysteine proteases is structurally well defined and determines the primary specificity of this protease class. For example, cathepsin B contains a glutamate (E245) residue at the bottom of the $S_2$ subsite pocket which favours the binding of basic residues like arginine. This glutamate residue is replaced by neutral residues in all other known human cathepsins resulting in a very low hydrolysis rate of the Z-R-R-MCA substrate. Cathepsin O2 contains a leucine residue in position 205 which makes Z-R-R-MCA a very poor substrate (FIG. 6). The specificity of cathepsin O2 towards $P_2$ residues resembles that of cathepsin S. Both enzymes prefer a leucine over a phenylalanine in this position while cathepsin L is characterized by an inverse specificity (Table 5, FIG. 6). Valine in position P2 is relatively well accepted by cathepsin O2, whereas the presence of this beta-branched residue in $P_2$ results in a poor substrate for cathepsins L, S and B.

TABLE II

Kinetic parameters for the Z-X-R-MCA catalyzed hydrolysis by recombinant human cathepsin O2

| Substrate | $k_{cat}$ (s$^{-1}$) | $K_m$ (µM) | $k_{cat}/K_m$ (M$^{-1}$s$^{-1}$) |
|---|---|---|---|
| Z-FR-MCA | 0.90 ± 0.20 | 7.5 ± 3.4 | 120,000 |
| Z-LR-MCA | 0.98 ± 0.39 | 3.8 ± 0.8 | 257,900 |
| Z-VR-MCA | 1.06 ± 0.16 | 13.1 ± 5.6 | 80,900 |
| Z-RR-MCA | 0.0005 ± 0.0002 | 23 ± 4 | 22 |
| Z-VVR-MCA | 0.01 ± 0.004 | 18.5 ± 1.5 | 540 |
| Z-LLR-MCA | 0.02 ± 0.008 | 0.4 ± 0.1 | 50,000 |

For the calculation of the kinetic parameters $k_{cat}$ and $K_m$ the initial rates were obtained typically at 9–11 different substrate concentrations, and the results are fitted to equation (1). The enzyme concentration is determined by active site titration with E-64 (Kinder et al., Biochem. J. 201:367–372 (1982)).

$$v = \frac{kcat \times E0 \times [S]}{(Km + [S])} \quad \text{equation (1)}$$

The catalytic efficiency ($k_{cat}/K_m$) of cathepsin O2 towards dipeptide substrates was comparable to that of cathepsins S and B, but was approximately one order of magnitude lower than that of cathepsin L. Interestingly, the $K_m$ values for cathepsin O2 were comparable to those determined for cathepsin L. The $K_m$ value reflects to some extent the affinity of the substrates for the protease. This trend is even more obvious for the tripeptide substrate, Z-LLR-MCA, which displays a $K_m$ value as low as $4\times10^{-7}$M (Table 5). However, in contrast to cathepsins S and L, the $k_{cat}$ values are almost two orders of magnitude lower for cathepsin O2, which may reflect non-productive binding.

Activities of Recombinant Human Cathepsin O2 Towards Extracellular Matrix Proteins

[$^3$H] elastin was prepared as described (Banda et al., Methods Enzymol. 144, 288–305 (1987)) and had a specific activity of 113,000 cpm/mg protein. Elastin (2 mg) was incubated in I ml buffer containing 2.5 mM dithiothreitol, 2.5 mM EDTA and 0.05% Triton X-100 for the cathepsin O2, S and L assays. Aliquots were withdrawn after 10, 20, 30, 50, 90, 120 and 180 min, centrifuged for 1 min at 14,000×g and counted in a 24-well plate containing scintillation fluid with Liquid Scintillation counter (1450 Microbeta Plus, Wallac/Pharmacia). Concentrations of human cathepsins O2, S and L and bovine elastase in the elastin degradation assay were 65 nM, 28 nM, 80 nM and 80 nM, respectively. To determine the pH effect on protease activity the digests were carried out at pH 4.5 and 5.5 (100 mM sodium acetate, 2.5 mM each dithiothreitol and EDTA, 0.05% Triton X-100), and at pH 7.0 (100 mM Tris/HCl, 2.5 mM each of dithiothreitol and EDTA, 0.05% Triton X-100). Pancreatic bovine elastase (Boehringer, Mannheim, Ind.) was assayed under the same conditions except that neither dithiothreitol nor EDTA was added to the incubation mixture.

Maximal activity was observed at pH 5.5. Cathepsin O2 has between pH 4.5 to 7.0 an elastinolytic activity which is 1.7 to 3.5 times higher than that of cathepsin S. Its elastinolytic activity at the pH optimum of cathepsin L (pH 5.5) and at neutral pH was almost 9-times and 2.4-times higher when compared to cathepsin L and pancreatic elastase, respectively (FIG. 7). The values determined for cathepsin L and S are in good accordance with published data (Kirschke et al., in: Proteolysis and Protein Turnover (Bond, J. S. and Barrett, A. J., eds.) pp 33–37, Portland Press, London and Chapel Hill (1993), Kirschke and Wiederanders, Methods Enzymol. 244, 500–511 (1994)).

Soluble calf skin Type I collagen was diluted to 0.4 mg/ml into 100 mM-sodium acetate buffer, pH 4.5, 5.0, 5.5, in 100 mM-potassium phosphate buffer, pH 6.0, 6.5 and 100 mM-Tris/HCl, pH 7.0 containing 2 mM-dithiotreitol/2 mM-EDTA. Human cathepsins O2, S and L and bovine trypsin (Sigma) were incubated at concentrations of 100 nM enzyme concentration for 10 hours at 28° C. To measure the gelatinase activity of cathepsins O2 and S, Type I collagen was heated for 10 min at 70° C. prior to incubation with the proteases. In the presence of 1 nM proteases the reaction mix was incubated for 30 min at 28° C. The samples were subjected to SDS polyacrylamide electrophoresis using 4–20% Tris-glycine gels (Novex, San Diego, Calif.).

Cathepsin O2 extensively degraded Type I collagen between pH 5.0 and 6.0 at 28° C. whereas the degradation at pH 4.5 and pH 7.0 is much less pronounced (FIG. 9a). The primary cleavage seemed to occur in the telopeptide region since the alpha monomers released from the beta and gamma components were slightly smaller. Additionally cleavage may also occur within the alpha monomers. It is yet unclear whether the cleavage occurrs in the intact helical region or in unraveled alpha monomers. Major fragments of Type I collagen observed after cathepsin O2 action had the size of 70–80 kDa. Cathepsin L also cleaved in the telopeptide region, but essentially no small molecular weight fragments were detected. The effective pH range for the collagenolytic activity of cathepsin L is more acidic when compared with that observed for cathepsin O2 (between pH 4.0 and 5.5). Cathepsin S seemed to reveal only a very weak collagenolytic activity. In contrast, tissue collagenases cleave the alpha monomers into 3/4 and ¼ fragments (Gross and Nagai, *Proc. Natl. Acad. Sci. U.S.A.* 54, 1197–1204 (1965)). No degradation of Type I collagen was observed with trypsin at equal enzyme concentration compared to cathepsin O2 showing that the integrity of the triple helix of the collagen used was not impaired (data not shown).

In addition to its collagenase activity cathepsin O2 displayed a powerful gelatinase activity. At 0.1 nM concentration of the enzyme, denatured collagen was totally degraded within 30 min within a pH range of 5.0 to 7.0. In contrast, cathepsin L displayed its gelatinase activity only in the pH range between 4.5–5.5 (FIG. 6b). Cathepsin S was active between pH 4.0 and 7.0, but displayed a significant weaker activity than the cathepsins O2 and L.

Relative elastinolytic activities of cathepsins compared with the bovine pancreatic elastase

| Protease | pH 4.5 mg/min/μmol enzyme | pH 5.5 mg/min/μmol enzyme | pH 7.0 mg/min/μmol enzyme |
|---|---|---|---|
| cathepsin O2 | 245 | 286 | 170 |
| cathepsin L | 18 | 32 | 0 |
| cathepsin S | 146 | 102 | 55 |
| pancreatic elastase | 8 | 18 | 79 |

Tissue Distribution of Human Cathepsin O2 on the Message Level

The tissue distribution of the message level of human cathepsins O2, L and S was determined by Northern blotting using cDNA probes of the appropriate human enzymes. The probes were approximately 450 base pairs long and stretched over the region coding for the residues between the active site residues cysteine-25 (according to the papain numbering) and asparagine-175. FIG. 8 shows Northern blots for human cathepsin O2. As shown in FIG. 8, message levels in human osteoclastoma preparations exhibit a many-fold higher level of expression of cathepsin O2 than cathepsin L.

The tissue distribution of human cathepsin O2 mRNA showed some similarities to cathepsin L, however, its tissue concentration seemed significantly lower in most of the organs (heart, placenta, lung, pancreas and kidney). On the other hand human cathepsin O2 displayed remarkable differences in its distribution in human tissues and cell lines when compared with the human cathepsins L and S. Cathepsin O2 showed high levels of transcription in ovary, small intestine and colon but no message in liver, which is rich for cathepsin L. It was also found in HeLa cells.

Tissue and cell line distribution (Northern Bolting)

| Tissue | HCATO | HCATL | HCATS |
|---|---|---|---|
| heart | xx | xxxx | — |
| brain | — | x | — |
| placenta | xx | xxxx | xx |
| lung | xx | xxx | xxx |
| liver | — | xxxx | xx |
| skeletal muscle | xx | xx | — |
| kidney | x | xxxx | — |
| pancreas | x | xx | — |
| spleen | x | — | x |
| thymus | x | x | — |
| prostate | x | x | — |
| testis | x | xx | — |
| ovary | xxx | x | — |
| small intestine | xx | — | — |
| colon | xxx | x | — |
| leukocytes | — | — | xxx |
| promyelocyt.leukemia HL-60 | — | — | x |
| HeLa S3 | xx | x | x |
| lymphoblast.leukemia MOLT-4 | — | xx | x |
| Burkitt's lymphoma Raji | — | — | x |
| colect.adenocarcinoma | — | x | — |
| lung carcinoma A549 | — | xxxx | x |
| melanoma G361 | — | xxxxx | — |

What is claimed is:

1. A recombinant enzymatically active cathepsin protein which has a polypeptide sequence consisting of amino acids 115–329 of SEQ ID NO:2.

2. The isolated polypeptide of claim 1 fused to a heterologous polypeptide.

3. A composition comprsing the isolated polypeptide of claim 1.

* * * * *